(12) United States Patent
Tang

(10) Patent No.: US 11,667,894 B2
(45) Date of Patent: *Jun. 6, 2023

(54) METHODS OF PRIMARY TISSUE CULTURE AND DRUG SCREENING USING AUTOLOGOUS SERUM AND FLUIDS

(71) Applicant: Yao Tang, Columbia, MD (US)

(72) Inventor: Yao Tang, Columbia, MD (US)

(73) Assignee: Yao Tang, Columbia, MD (US)

( * ) Notice: Subject to any disclaimer, the term of this patent is extended or adjusted under 35 U.S.C. 154(b) by 331 days.

This patent is subject to a terminal disclaimer.

(21) Appl. No.: 16/921,007

(22) Filed: Jul. 6, 2020

(65) Prior Publication Data

US 2020/0347361 A1    Nov. 5, 2020

Related U.S. Application Data

(63) Continuation of application No. 15/075,332, filed on Mar. 21, 2016, now Pat. No. 10,745,667.

(51) Int. Cl.
*C12N 5/09* (2010.01)

(52) U.S. Cl.
CPC .......... *C12N 5/0694* (2013.01); *C12N 5/0693* (2013.01); *C12N 2500/84* (2013.01); *C12N 2503/02* (2013.01); *C12N 2509/00* (2013.01); *C12N 2509/10* (2013.01); *C12N 2513/00* (2013.01); *C12N 2533/52* (2013.01); *C12N 2533/54* (2013.01); *C12N 2533/90* (2013.01)

(58) Field of Classification Search
CPC ............ C12N 2500/84; C12N 2503/02; C12N 2509/00; C12N 2509/10; C12N 2513/00; C12N 2533/52; C12N 2533/54; C12N 2533/90; C12N 5/0693; C12N 5/0694
See application file for complete search history.

(56) References Cited

U.S. PATENT DOCUMENTS

| | | | | |
|---|---|---|---|---|
| 5,443,950 A | * | 8/1995 | Naughton | A61L 27/60 424/572 |
| 6,893,812 B2 | * | 5/2005 | Woltering | G01N 33/5088 435/395 |
| 10,745,667 B2 | * | 8/2020 | Tang | C12N 5/0693 |

* cited by examiner

*Primary Examiner* — Blaine Lankford

(57) ABSTRACT

The present invention provides methods for culturing primary cells and tissues from a subject in the presence of the subject's own serum, ascites or pleural effusion fluid. Methods of treating cancer, and screening for the effectiveness or toxicity of drugs are also provided herein.

8 Claims, 14 Drawing Sheets

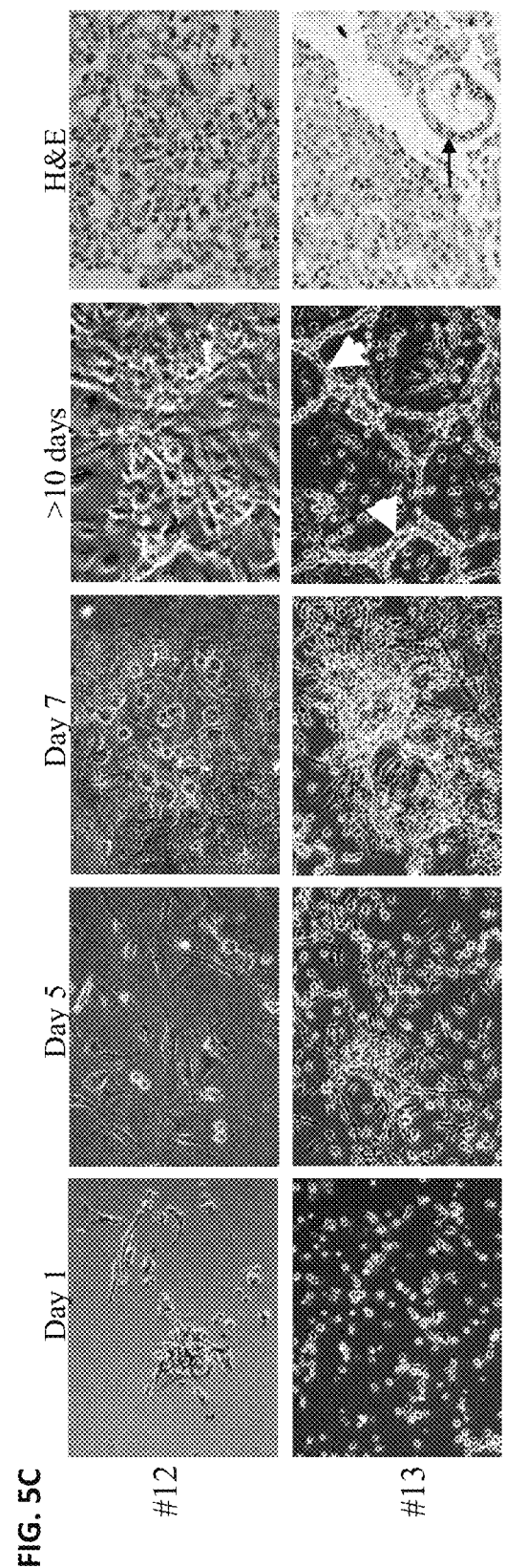

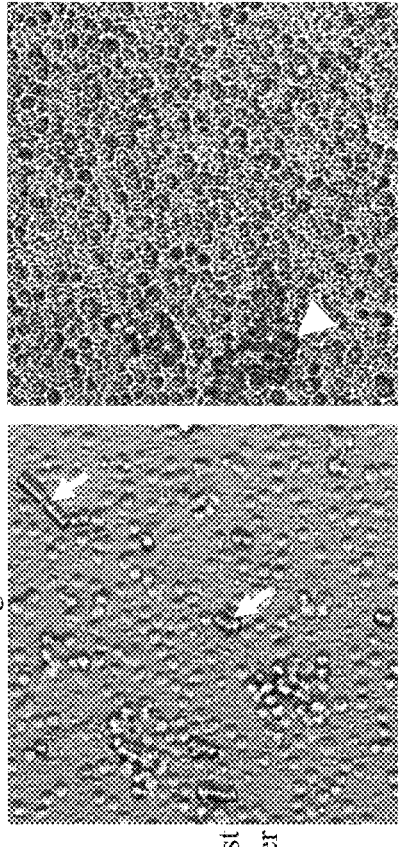 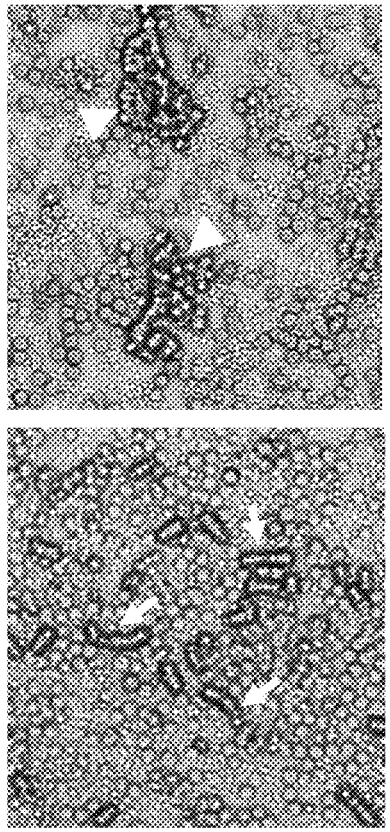
FIG. 8A Breast cancer
FIG. 8B Stomach cancer
48 hours (20x)
Autologous HS
FBS

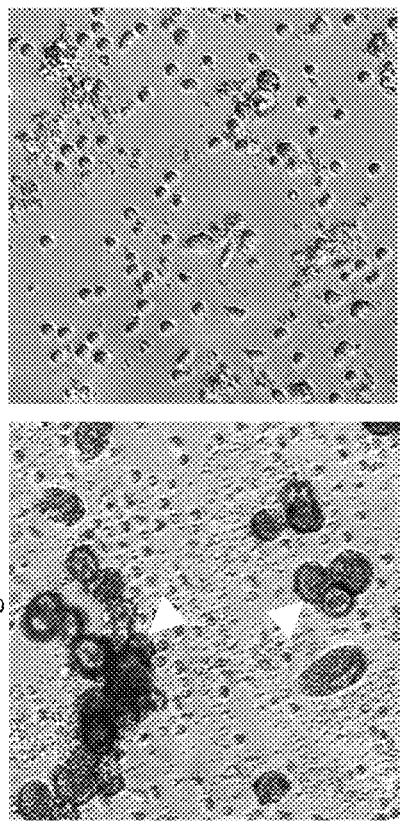
FIG. 8C Breast cancer
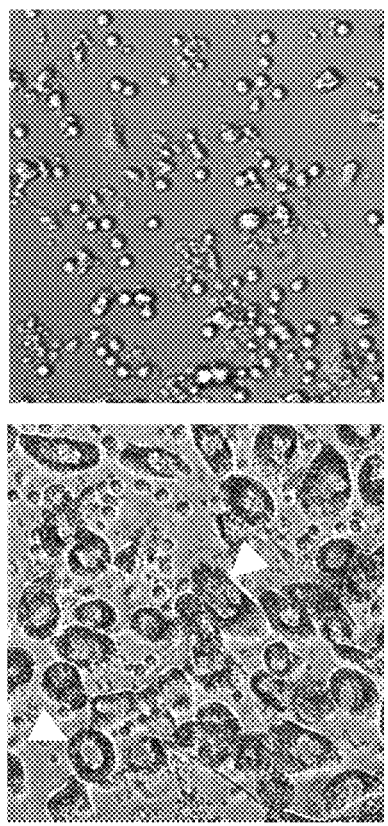
FIG. 8D Stomach cancer

METHODS OF PRIMARY TISSUE CULTURE AND DRUG SCREENING USING AUTOLOGOUS SERUM AND FLUIDS

CROSS REFERENCE TO RELATED APPLICATIONS

This application claims the benefit of U.S. Provisional Appl. No. 62/137,218, filed Mar. 23, 2015. The content of the aforesaid application is relied upon and incorporated by reference in their entireties.

FIELD OF THE INVENTION

The field of the invention relates to cell biology and medicine.

BACKGROUND OF THE INVENTION

Scientists have long sought to improve culturing systems to support medical research in general, and treatment, including cancer treatment, in particular. However, cancer patients are highly individualized in their response to chemotherapies or other anti-cancer regimens. The success of individualized therapy requires accurate pre-testing to determine drug-sensitivity, no matter if the target is DNA, protein, enzyme, hormone or cytoskeleton. In turn, accurate pre-testing requires a tumor sample growing in a microenvironment that is maximally similar to its original condition. Tumor cells grow as 'seeds' in their microenvironment, which functions as the 'soil'. If the 'soil' is not well-suited to the growth of the tumor cells, death or biological alterations occur. Although many efforts have been made in this field, a challenge remains regarding the creation of in vitro environments that are suitable for all types of tumors, from different individuals (See Edmondson R et al., Assay & Drug Development Technologies. 2014; 12(4): 207-218.; Garcia-Posadas et al., Invest Ophthalmol Vis Sci. 2013; 54(10): 7143-7152; Ravi M et al., J Cell Physiol. 2015; 230(1):16-26; Thoma C R et al., J Biomol Screen. 2013; 18(10):1330-1337; Tsai M J et al., Hindawi Publishing Corporation, ISRN Biochemistry. 2014; 2014:1-8; Wu M et al., J Biomech Eng. 2014; 136(2): 021011).

For decades, scientists have been using two-dimensional (2D) cell culture studies in attempting to understand tumor biology, function, and pathology. Many chemo-sensitivity tests have been developed based on the 2D culture system. Although these culture systems have produced many important advances, cells grown in 2D conditions can differ considerably in their morphology, cell-cell and cell-matrix interactions and the process of differentiation, from those grown in physiological environments. Three-dimensional (3D) culture models have been developed for cell lines and cells dissociated from tissues (See Birgersdotter A et al., Semin Cancer Biol. 2005; 15(5):405-412; Cukierman E et al., Curr Opin Cell Biol. 2002; 14(5):633-639; Griffith L G et al., Nat Rev Mol Cell Biol. 2006; 7(3):211-224; Nelson C M et al., Annu Rev Cell Dev Biol. 2006; 22:287-309).

Cancer studies have long focused on cloned cancer cells (i.e., established cell lines). Recently, however, the tumor microenvironment has been increasingly recognized as a key contributor to cancer progression and drug resistance (See Heinrich E L et al., Cancer Microenviron. 2012; 5(1):5-18). In the tumor microenvironment (the cellular environment in which the tumor exists) there are blood vessels, immune cells, fibroblasts, signaling molecules, and other mesenchymal cells, as well as the extracellular matrix (ECM). The tumor and its surrounding cells and matrix are closely related and communicate constantly. Tumors can influence the microenvironment by releasing extracellular signals, promoting angiogenesis and inducing peripheral immune tolerance, while the immune cells in the microenvironment can affect the growth, behavior, and evolution of cancerous cells (See Tsai M J et al., Hindawi Publishing Corporation, ISRN Biochemistry. 2014; 2014:1-8; Wu M et al., J Biomech Eng. 2014; 136(2):021011; Allinen M et al., Cancer Cell. 2004; 6(1):17-32; Bhat R et al., Wiley Interdiscip Rev Dev Biol. 2014; 3 (2): 147-163; Bissell M J et al., Cold Spring Harb Symp Quant Biol. 2005; 70:343-356). The tumor microenvironment has also been shown to contribute to tumor heterogeneity (See Wu M et al., J Biomech Eng. 2014; 136(2):021011; Yamada K M et al., Cell. 2007; 130(4): 601-610).

In one attempt to mimic the tumor microenvironment, immortalized stroma cells (fibroblast, endothelial) were mixed with cancer cells in the culture (See Thoma C R et al., J Biomol Screen. 2013; 18(10):1330-1337; Fu W et al., Chung-Kuo Hsiu Fu Chung Chien Wai Ko Tsa Chih/Chinese Journal of Reparative & Reconstructive Surgery. 2014; 28(2):179-185). A more recent study has shown that using irradiated stroma cells as the feeder layer in cultures can help tumor cells re-build their histologic structure (See Saenz F R et al., PLoS One. 2014; 9(5):e97666). But because the source of these stroma cells is either biologically different from the tumor cells or has lost the function to communicate with tumor cells (after irradiation), these artificial microenvironments do not closely represent conditions in the patient.

In addition to cellular effects, molecular biochemistry plays another important role in the microenvironment of a tumor. The pleiotropic nature of cytokines in the microenvironment contributes to promoting cancer cell proliferation, bypassing apoptosis, inducing the EMT (epithelial-mesenchymal-transition) of cancer cells, enhancing chemokines to recruit immune suppressor cells that aggregate around the tumor, and even driving the development of drug resistance (See Shain K H et al., Expert Rev Hematol. 2009; 2(6):649-662). Increasing evidence demonstrates that a variety of inflammatory mediators from cancer and tumor-infiltrating cells, such as IL-1, IL-6, and IL-8, facilitate the development of a tumor microenvironment that favors tumor cell proliferation, motility and invasion, and thereby increases their metastatic potential (See O'Callaghan D S et al., J Thorac Oncol. 2010; 5(12):2024-2036; Gilbert C A et al., Annu Rev Med. 2013; 64:45-57). All of these in vivo factors make the selection of a cancer therapy for an individual much more complicated and challenging.

Human blood supplies in vivo bring large amount of nutrients as well as necessary cytokines, chemokines, growth factors, and hormones supporting tumor growth. In current 2D and 3D culture systems, these nutrients are supplied by 5-20% fetal bovine serum (FBS). Although cytokines/growth factors have been manually added into certain culture systems to support and/or maintain the growth of tumor cells in vitro (See Saenz F R et al., PLoS One. 2014; 9(5):e97666; Kobayashi H et al., Int J Oncol. 1997; 11(3):449-455; Kobayashi H, Recent Results Cancer Res. 2003; 161:48-61; Kobayashi H, Methods Mol Med. 2005; 110:59-67; Nakagawa T et al., Gan To Kagaku Ryoho. 2004; 31(13):2145-2149), these artificial conditions could be very different from those in an individual patient. The use of human blood to culture human cells has also been researched; however, previous studies have employed pooled normal human serum (commercially provided) rather than individualized (See Isaac C et al., *Rev Bras Cir Plast.* 2011; 26 (3):379-384). Significantly different gene/protein expressions are observed between cells cultured with FBS versus human serum. Even within an individual, blood chemistry varies with a patient's physiological condition, as well as the type and stage of their disease (See Whitney A R. et al., *Proc Natl Acad Sci USA.* 2003; 100(4):1896-1901; Baine M J et al., *Methods Mol Biol.* 2013; 980:157-173; Chen Y et al., *J Cancer Res Clin Oncol.* 2014).

Because in vitro cell culture systems lack the relevant physiological characteristics necessary for drug evaluation, the investigation of efficacy through in vivo models (e.g., murine models) has been widely accepted. However, implanting a human tumor into an animal results in an abrupt change in the microenvironment of the tumor, forcing the tumor cells to attempt to communicate with stroma cells from a different species. In addition, the high financial cost of animal experimentation mitigates against its widespread clinical use.

Tumors shed cells that can enter the bloodstream. These are called circulating tumor cells (CTCs) which can take root elsewhere, causing the spread of the cancer (See Castle J et al., *The Breast.* 2014; 23(5):552-560; Kolostova K et al., *Am J Transl Res.* 2015; 7(7):1203-1213; Eliasova P et al., *Folia Histochem Cytobiol.* 2013; 51(4):265-277; Friedlander T W et al., *J Clin Oncol.* 2014; 32(11):1104-1106; Friedlander T W et al., *Pharmacol Ther.* 2014; 142(3):271-280). There is considerable interest in CTC research and technologies for their potential use as cancer biomarkers that may enhance cancer diagnosis and prognosis, facilitate drug development, and improve the treatment of cancer patients. (See Harouaka R et al., *Pharmacol Ther.* 2014; 141(2):209-221). The isolation and analysis of CTCs are useful methods for tracking how cancers evolve during disease progress and therapy. However, because these cells occur in very low numbers and circulate through the body, isolating CTCs from the blood of cancer patients has been a technical challenge (See Castle J et al., *The Breast.* 2014; 23(5):552-560; Kolostova K et al., *Am J Transl Res.* 2015; 7(7):1203-1213; Eliasova P et al., *Folia Histochem Cytobiol.* 2013; 51(4):265-277; Friedlander T W et al., *J Clin Oncol.* 2014; 32(11):1104-1106; Friedlander T W et al., *Pharmacol Ther.* 2014; 142(3):271-280).

It is well-known that, to date, drugs are usually much more effective in experimental studies (both in vitro and in vivo) than in actual clinical practice. An approach for individualized drug-sensitivity testing was created by Dr. Hisayuki Kobayashi, a technique which has undergone clinical trials (See Kobayashi H, *Recent Results Cancer Res.* 2003; 161:48-61; Kobayashi H, *Methods Mol Med.* 2005; 110: 59-67; Higashiyama M et al., *Lung Cancer.* 2010; 68(3):472-477; Higashiyama M et al., *J Thorac Dis.* 2012; 4(1):40-47; Higashiyama M et al., *Ann Thorac Cardiovasc Surg.* 2008; 14(6):355-362; Kawamura M et al., *Cancer Chemother Pharmacol.* 2007; 59(4):507-513; Nagai N et al., *Anticancer Drugs.* 2005; 16(5):525-531; Naitoh H et al., *Gastric Cancer.* 2014; 17(4):630-637; Tanioka M et al., *Exp Ther Med.* 2010; 1(1):65-68). This technique is named CD-DST (the collagen gel droplet embedded culture-drug sensitivity test (See Kobayashi H et al., *Int J Oncol.* 1997; 11(3):449-455; Kobayashi H et al., *Int J Oncol.* 1997; 11(3):449-455)). The working principle of this technique is to culture cancer cells from individual patients in a 3D environment for a relatively short time (15-20 days), but long enough for drug testing. Tumors from different patients are cultured under the same artificial conditions, basically with a nutrient supply consisting of 10% FBS-complemented commercial culture media plus some growth factors (See Saenz F R et al., *PLoS One.* 2014; 9(5):e97666). The drug sensitivity testing is performed in a microenvironment that is far different from the tumor's natural condition. Accordingly, the results of testing with this culture system may not accurately predict the response of the tumor when the drug is administered to the patient. Additionally, use of 2% autologous serum in a culture medium also having 8% FBS has also been described (Majumder B et al., *Nature Communications* 2015; 6:1-14). Commercial growth factors and special antibodies were also added into these cultures. Such a culture medium is far different from a patient's real condition.

Thus, there is a need for improved culture methods that more closely replicate in vivo conditions.

This background information is provided for informational purposes only. No admission is necessarily intended, nor should it be construed, that any of the preceding information constitutes prior art against the present invention.

SUMMARY OF THE INVENTION

It is well-known that, to date, drugs are usually much more effective in experimental studies (both in vitro and in vivo) than in actual clinical practice. It is hypothesized that this is due to differences in the growth conditions that cells and tissues encounter in experiments as compared to those in patients, specifically regarding the structural platform and the microenvironment.

The invention is based on the discovery of protocols for cell culturing which utilize a subject's own serum or body fluid and which closely mimic the cellular or tissue microenvironment. In some embodiments, a cancer patient's own serum is used to grow his/her cancer cells in a 3D culture condition. Other cells that surround the tumor or co-exist in the cancerous fluid can also survive in this system. With the methods of the invention, tumor cells remain in a microenvironment that is virtually identical to the one they experienced inside of the patient, with similar nutrients and biochemical supplies. The present invention provides for more accurate drug sensitivity testing to improve the effectiveness of individualized cancer therapy. In some embodiments, the methods use the patient's body fluid to culture their own tumors in vitro, including solid tumors, malignant serous tumors, peripheral blood mononuclear cells (PBMCs) and circulating tumor cells (CTCs), as well as stromal cells associated with the tumors. This greatly increases the success rate of primary culture for human cancers. In some embodiments, one difference from traditional cell cultures is that, in the present culture system, tumor cells and their autologous surrounding tissue cells survive and grow together, and are able to reconstruct the tumor's original histopathology structures. Because of the similarity in the in vivo and ex vivo microenvironments, no change in immunophenotypes was found in tumor tissues before and after cultures. In addition, human PBMCs also survived well for at least 4-5 days and CTCs in the blood circulation can be multiplied in this culture system. This culture technique can have many applications, including, but not limited to: (1) the study of cancer as a complete tissue instead of isolated cancer cells; (2) chemo-sensitivity testing with improved accuracy; (3) evaluation of the toxicity of a drug to PBMCs, (4) in vitro multiplication of CTCs in a patient's blood and; (5) provision of a new platform for other pre-clinical targeted therapies (e.g. gene-therapy or immunotherapy) for cancerous or non-cancerous diseases, to improve the accuracy and efficacy of individualized/personalized treatment.

According to non-limiting example embodiments, in one aspect, the invention provides a method of culturing solid tissue from a subject, comprising
 i) obtaining the solid tissue from the subject;
 ii) obtaining serum from the subject; and
 iii) culturing the tissue in a three-dimensional biocompatible matrix in the presence of a media comprising at least 50% serum (v/v) from the subject.

In another aspect, the invention provides a method of culturing primary cells from ascites fluid from a subject comprising
 i) obtaining the cells from ascites fluid from the subject;
 ii) seeding the cells on a surface of a biocompatible matrix; and
 iii) culturing the cells in a media comprising ascites fluid from the subject.

In another aspect, the invention provides a method of culturing primary cells from pleural effusion fluid from a subject comprising
 i) obtaining the cells from pleural effusion fluid from the subject;
 ii) seeding the cells on a surface of a biocompatible matrix; and
 iii) culturing the cells in a media comprising pleural effusion fluid from the subject.

In another aspect, the invention provides a method of culturing cells from blood from a subject comprising
 i) obtaining the cells from the blood of the subject;
 ii) obtaining serum from the subject; and
 iii) culturing the cells in the presence of a media comprising at least 50% serum (v/v) from the subject.

In another aspect, the invention provides a method for testing the effectiveness or toxicity of a therapeutic agent, comprising:
 i) culturing cells or solid tissue from a subject according to the methods of the invention;
 ii) contacting the cultured cells or solid tissue with the therapeutic agent; and
 iii) assessing the effectiveness or toxicity of the therapeutic agent as a treatment for the subject.

In another aspect, the invention provides a method of treating cancer in a subject, comprising
 i) culturing cancer cells or solid cancer tissue from a subject according to the methods of the invention;
 ii) contacting the cultured cells or solid tissue with a therapeutic agent;
 iii) assessing the effectiveness or toxicity of the therapeutic agent as a treatment for the subject; and
 iv) administering to the subject an effective amount of the therapeutic agent.

In another aspect, the invention provides a method of screening for anti-cancer agents, comprising
 i) culturing cells or solid tissue from a subject according to the methods of the invention;
 ii) contacting the cells or solid tissue with one or more candidate anti-cancer agents; and
 iii) assessing the effectiveness or toxicity of the candidate anti-cancer agent as a cancer treatment.

In another aspect, the invention provides a method of enriching circulating tumor cells in a population of blood cells, comprising
 i) obtaining a cell fraction comprising PBMCs from the blood of the subject;
 ii) obtaining serum from the subject; and
 iii) culturing the cells in the presence of serum from the subject for a period of time whereby the CTCs are enriched in the cell population.

In another aspect, the invention provides a method for simultaneously testing the toxicity and effectiveness of a therapy in order to select the treatment that is suitable for a subject, comprising
 i) culturing solid tissue or cells according to the following
  1. obtaining the solid tissue from the subject;
  2. obtaining serum from the subject; and
  3. culturing the tissue in a three-dimensional biocompatible matrix in the presence of a media comprising at least 50% serum (v/v) from the subject; or
 ii) culturing cells according to the following
  1. obtaining the cells from ascites or pleural effusion fluid from the subject;
  2. seeding the cells on a surface of a biocompatible matrix; and
  3. culturing the cells in a media comprising ascites or pleural effusion fluid from the subject; and
 iii) contacting the cells or solid tissue with one or more candidate therapeutic agents;
 iv) assessing the effectiveness of the candidate therapeutic agent of iii);
 v) culturing PBMC according to the following;
  1. obtaining the PBMC from the blood of the subject;
  2. obtaining serum from the subject; and
  3. culturing the PBMC in the presence of a media comprising at least 50% serum (v/v) from the subject; and
 vi) contacting the PBMC with the one or more candidate therapeutic agents of iii);
 vii) assessing the toxicity of the candidate therapeutic agent on the PBMC; and
 viii) administering to the subject the therapeutic agent that exhibits a suitable profile for effectiveness and toxicity.

It is to be understood that both the foregoing general description and the following detailed description are exemplary, and thus do not restrict the scope of the invention. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

FIG. 8. Comparison of blood cell cultures in autologous serum (HS) and fetal bovine serum (FBS). (A) Photomicrographs of PBMC from a breast cancer patient cultured for 48 hours in autologous HS (top left) and in FBS (top right). (B) Photomicrographs of PBMC from a stomach cancer patient cultured for 48 hours in autologous HS (bottom left) and in FBS (bottom right). Light green arrows in (A) and (B) indicate relatively healthy red blood cells in lines, in the HS cultures. Red arrow-heads in (A) and (B) indicate aggregation of damaged red blood cells in FBS. (C) Photomicrographs of PBMC from a breast cancer patient cultured for 6 days in autologous HS (top left) and in FBS (top right). (D) Photomicrographs of PBMC from a stomach cancer patient cultured for 6 days in autologous HS (bottom left) and in FBS (bottom right). Light green arrows in (C) and (D) indicate enriched tumor cells (CTCs).

DETAILED DESCRIPTION

Figure 1:
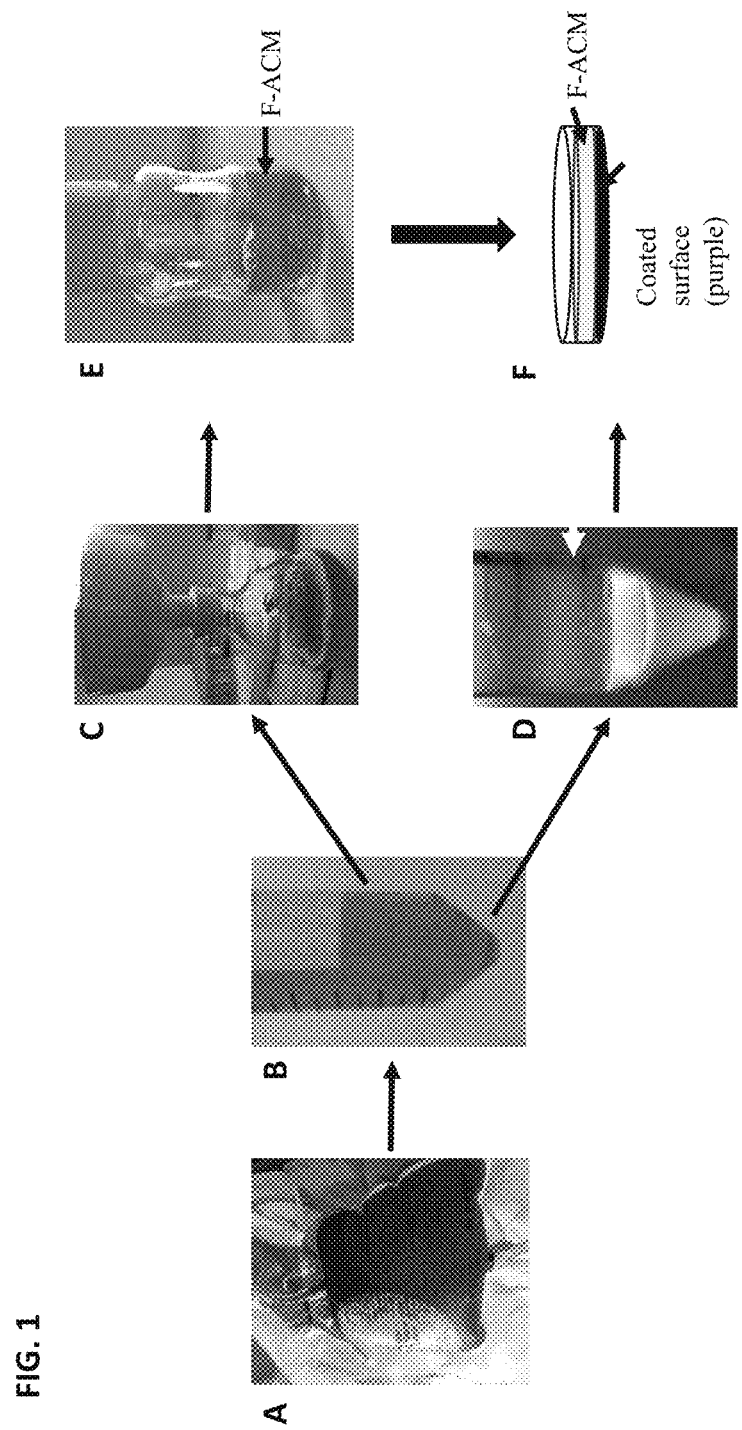
FIG. 1. Procedure for making ascites and pleural effusion fluid and cell samples. (A) Ascites and pleural effusion samples were collected. (B) The ascites and pleural effusion samples are aliquoted into 50-ml tubes and centrifuged to precipitate cells. (C) The resultant supernatants were further cleaned (Step C). (D) The precipitated cells were re-suspended in PBS and uploaded on FICOLL (Density Gradient Centrifugation Media) and centrifuged again to remove red blood cells (the white arrow signifies the enriched cell layer). (E) The supernatants were pooled following the cleaning step as f-ACM. (F) Fifty thousand cells from the enriched layer ($5\times10^5$)/plate in 10 ml of autologous f-ACM were seeded on top of the polymerized gel and the medium (f-ACM) was refreshed every 3-4 days.

The ex vivo culturing technique of the present invention use the patient's body fluid or serum to culture the patient's own cells or tissues, such as tumor tissue or cancer cells. It can be used to culture solid tumors, tumors from malignant effusion (ascites and pleural fluids) and PBMC as well as CTCs. Because this technique creates an external environment that mimics the tumor's internal condition (inside of a patient), it makes it possible, for the first time, to grow a tumor ex vivo not just as tumor cells but as a tissue, with a high rate of success. This provides a reliable platform for precision, individualized medicine and is expected to greatly improve the accuracy of drug-sensitivity test for an individual patient.

In some embodiments, one difference of this technique compared with traditional cell cultures is that tumor cells and their autologous surrounding tissue cells survive and grow together in their own body solutions, which enables them to reconstruct the tumor's original histopathology structures. Because of this similarity in the tumor's in vivo and ex vivo microenvironments, no change in immunophenotypes was found in tumor tissues before and after cultures.

The applications of this invention include, but are not limited to:

(1) supporting the study of cancer as a complete tissue in lab research, instead of cancer cells alone (current status). It provides a new platform for scientists to study the cellular communications of tumor-to-tumor and tumor-stromal cells in real-time.

(2) improving the accuracy of drug-sensitivity tests. Since the tumor grows in a microenvironment similar to its original condition, the reaction to medical treatment in this culture system should more correctly predict the real therapeutic response of the tumor in the patient. In addition, because tumor tissues can survive in the culture for at least 8-10 days, it makes it possible to functionally profile a living tumor's reactions after exposure to drug(s).

(3) enabling the comparison of the toxicity of tumor cells and PBMCs side-by-side to a given drug. Since "normal" PBMCs also survive in this system for at least 4-5 days, drug-sensitivity testing can be simultaneously conducted on patient's tumor cells and PBMCs to compare their toxicities to the same given drug(s). This procedure will prevent or greatly reduce negative side-effects to cancer patients of potential therapies.

(4) increasing the CTC population for treatment and study. The rare population of CTC can be efficiently expanded in this culture system. Since they are living and proliferating in their own serum, they can also be used for functional tests and drug sensitivity tests.

(5) providing a new platform for other types of preclinical treatment tests. Since no anti-cancer regimes, including various targeted therapies (e.g. gene-therapy or immunotherapy), can fit all cancer patients, they should be tested prior to use in a particular patient. This culture system can also be employed for these tests, to improve the accuracy and efficacy of individualized/personalized treatment.

(6) studying, and testing of therapies for, non-cancerous diseases. Because "normal" stromal cells (existing in tumor surrounding tissue) including endothelial, fibroblast, mesothelial and cartilage, can also survive in this system for 7-10 days, this technique makes it possible to conduct studies and treatment tests on non-cancer diseases.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

Culturing Solid Tissue in Autologous Serum

In one embodiment, the invention provides a method of culturing solid tissue from a subject, comprising
 i) obtaining the solid tissue from the subject;
 ii) obtaining serum from the subject; and
 iii) culturing the tissue in a three-dimensional biocompatible matrix in the presence of a media comprising at least 50% serum (v/v) from the subject.

The solid tissue that can be cultured according to the methods of the invention is not limiting. In some embodiments, the solid tissue comprises normal healthy tissue. In some embodiments, the solid tissue comprises diseased tissue. In some embodiments, the solid tissue comprises tissue isolated from a tumor. In some embodiments, the tissue comprises cancerous and noncancerous cells, such as stromal cells. The tissue and cells that are isolated from a solid tumor are primary tissue and cells. In some embodiments, the solid tissue comprises tissue isolated from a subject having a disease.

In some embodiments, the solid tissue comprises tissue isolated from a tumor. The tissue isolated from a tumor is not limiting. In some embodiments, the isolated tumor tissue is selected from the group consisting of lung cancer tissue, stomach cancer tissue, colon cancer tissue, lymph node metastatic cancer tissue, melanoma tissue, renal cell carcinoma tissue, squamous non-small cell lung (NSCLC) tissue, non-squamous NSCLC tissue, rectal cancer tissue, prostate cancer tissue, ovarian cancer tissue, hepatocellular carcinoma tissue, pancreatic carcinoma tissue, squamous cell carcinoma tissue of the head and neck, esophageal cancer tissue, gastrointestinal tract cancer tissue, breast cancer tissue, bone cancer tissue, brain cancer tissue, thyroid cancer tissue, testicular cancer tissue and vaginal cancer tissue.

In some embodiments, the tissue is isolated directly from a non-removed tumor, from a tumor biopsy, or from a tumor that is surgically removed. In some embodiments, the isolated tissue is grown in another animal, such as a mouse, (tumorgrafts, PDX), isolated from the animal and then analyzed.

In some embodiments, the solid tissue is isolated by mechanical means, such as dissection, from the subject. In some embodiments, the solid tissue is not subjected to enzymatic digestion prior to culturing. In some embodiments, the solid tissue is surgically removed and cut into small pieces for use in the culturing method of the invention. In some embodiments, the solid tissue is cut into pieces having a diameter of less than about 1 mm, less than about 0.75 mm, less than about 0.5 mm or less than about 0.25 mm.

The method for obtaining serum from the subject for use in the invention can be by conventional means and is not limiting. In some embodiments, 15-ml of fresh blood without anti-coagulant is withdrawn from each patient before and is stored at room temperature until coagulation is complete. In some embodiments, about 5 ml, 10 ml, 15 ml, 20 ml or 25 ml of fresh blood without anti-coagulant is withdrawn from each patient before and is stored at room temperature until coagulation is complete. The blood can be centrifuged and the serum isolated. In some embodiments, one or more antibiotics can be added to the serum. The antibiotic that can be added is not limiting. In some embodiments, the antibiotic is one that is commonly used in cell culture techniques, such as, for example, penicillin or streptomycin. In some embodiments cefoperazone is added to the serum (Pfizer Dalian Pharmaceutical Plant) to a final concentration of 20 µg/ml.

In some embodiments, the tissue is cultured in a media comprising 50-100% serum (v/v) from the subject. In some embodiments, the tissue is cultured in a media comprising about 50%, 55%, 60%, 65%, 70%, 75%, 80%, 85%, 90%, 95%, or 100% serum (v/v) from the subject. In some embodiments, a base media is combined with the subject's serum. The base media is not limiting and can include, for example, saline, phosphate buffered saline, Dulbecco's Modification of Eagle's Medium (DMEM), Ham's F-12 (F12), Ham's F-10 (F10), RPMI 1640, Iscove's Modified Dulbecco's Medium (IMDM) or a combination thereof. In some embodiments, the media comprises a 1:1 mixture of the subject's serum and RPMI 1640. In some embodiments, the media comprises about a 1:1, 2:1, 3:1 or 4:1 (v/v) mixture of the subject's serum and RPMI 1640. In some embodiments, exogenous factors, such as antibodies, growth factors, cytokines, or FBS are not added to media and the tissue is nourished primarily by the natural body fluid without artificial modification.

In accordance with the invention, the subject's solid tissue is cultured in a three-dimensional biocompatible matrix in the presence of the subject's serum. The three-dimensional biocompatible matrix is not limiting. In some embodiments, the three-dimensional biocompatible matrix replicates or mimics the extracellular matrix (ECM). In some embodiments, the three-dimensional biocompatible matrix can comprise a scaffold-free platform for spheroid growth, scaffold, gel, bioreactor, or microchip.

In some embodiments, the three-dimensional biocompatible matrix comprises one or more cell matrix proteins. In some embodiments, the cell matrix proteins comprise one or more of laminin, entactin, collagen, nidogen, or heparan sulfate proteoglycans.

In some embodiments, the three-dimensional biocompatible matrix comprises a gel. In general, gels have a soft tissue-like stiffness and aim to mimic the ECM. Gels made from ECM mixtures of natural origin, such as collagen, and alginate, have been used as substrates for 3D cell culture. In some embodiments, the gel is MATRIGEL. MATRIGEL is a reconstituted basement membrane preparation extracted from the Engelbreth-Holm-Swarm mouse sarcoma, a tumor rich in ECM proteins, such as laminin and collagen, plus growth factors and enzymes. MATRIGEL is produced and marketed by Corning Life Sciences. MATRIGEL contains approximately 60% laminin, 30% collagen IV, and 8% entactin. In some embodiments, the three-dimensional biocompatible matrix comprises MATRIGEL.

Culturing times and conditions are not limiting. In some embodiments, the cells are cultured for 3-4 days and then the media is refreshed. In some embodiments, the cells can be cultured for at least 1, 2, 3, 4, 5, 6, 7, 8, 9, 10, 11, 12, 13, 14, 15, 20 or 30 days.

In some embodiments, the method comprises
coating a culture surface with a first composition comprising one or more types of cell matrix proteins;
placing the solid tissue onto the coated surface;
adding a second composition comprising one or more types of cell matrix proteins to the solid tissue, so that the solid tissue is immersed in the second composition and polymerizing the second composition to form the three-dimensional biocompatible matrix; and
adding the serum to the immersed solid tissue and culturing the tissue.

In some embodiments, the first composition comprises MATRIGEL or a mixture of MATRIGEL and serum from the subject. In some embodiments, the first composition comprises a 1:1 (v/v) mixture of the subject's serum and MATRIGEL. In some embodiments, the first composition comprises about a 1:1, 1:2, 1:3 or 1:4 (v/v) mixture of the subject's serum and MATRIGEL. The first composition can comprise the three-dimensional biocompatible matrix described herein.

The thickness of the coating of the first composition is not limiting. In some embodiments, the coating has a thickness less than or equal to 0.5 mm. In some embodiments, the coating has a thickness of about 0.5 mm, 0.4 mm, 0.3 mm, 0.2 mm or 0.1 mm. In some embodiments, the coating has a thickness of about 0.1 to 0.4 mm.

In some embodiments, the second composition comprises MATRIGEL, or a mixture of MATRIGEL and serum from the subject. In some embodiments, the second composition comprises a 1:1 (v/v) mixture of the subject's serum and MATRIGEL. In some embodiments, the second composition comprises about a 1:1, 1:2, 1:3 or 1:4 (v/v) mixture of the subject's serum and MATRIGEL. The second composition can comprise the three-dimensional biocompatible matrix described herein.

Culturing Primary Cells from Ascites Fluid in Autologous Ascites Fluid

In one embodiment, the invention provides a method of culturing primary cells from ascites fluid from a subject comprising
i) obtaining the cells from ascites fluid from the subject;
ii) seeding the cells on a surface of a biocompatible matrix; and
iii) culturing the cells in a media comprising ascites fluid from the subject.

Ascites fluid can be collected from the patient in any suitable amount. In some embodiments, 100-2000 ml of ascites fluid is collected from the patient. In other embodiments, 500-800 ml ascites fluid is collected from the patient. Cells can be obtained from the ascites fluid by any suitable means including centrifugation, density gradient centrifugation and filtration. In some embodiments, cells present in the collected ascites fluid are pelleted by centrifugation, resuspended in PBS, subjected to density gradient centrifugation in FICOLL, washed in PBS and re-suspended in media comprising autologous ascites fluid. In some embodiments, other types of density gradient centrifugation media can be used, like PERCOLL. In some embodiments, centrifugation is performed at 2000 rpm.

Any suitable amount of cells from ascites fluid can be seeded on the surface of the bio-compatible matrix. In some embodiments, about $1\times10^5$, $2\times10^5$, $3\times10^5$, $4\times10^5$, $5\times10^5$, $6\times10^5$, $7\times10^5$, $8\times10^5$, $9\times10^5$, or $1\times10^6$ cells are seeded on the surface of a biocompatible matrix coating a 100 mm culture dish or other type of culture plate or dish.

The cells can comprise noncancerous or cancerous cells and is not limiting. In some embodiments, the cells comprise cancer cells. The cancer cells can comprise stomach cancer cells, endometrium cancer cells, ovarian cancer cells, breast cancer cells, pancreatic cancer cells, uterine cancer, colon cancer cells, melanoma cells, leukemia cells, or lymphoma cells. The cells can comprise a mixed population of cells present in the ascites fluid. The mixed population can comprise cancer cells, blood cells and mesothelial cells at various proportions.

The biocompatible matrix is not limited. In some embodiments, the biocompatible matrix comprises one or more cell matrix proteins. In some embodiments, the cell matrix proteins comprise one or more of laminin, entactin, collagen, nidogen, or heparan sulfate proteoglycans.

In some embodiments, the biocompatible matrix comprises a gel. In some embodiments, the biocompatible matrix comprises a gel and autologous ascites fluid. In some embodiments, the gel is MATRIGEL. In some embodiments, the biocompatible matrix comprises a mixture of MATRIGEL and autologous ascites fluid. In some embodiments, the biocompatible matrix comprises a 1:1, 1:2, 1:3, 1:4, 2:1, 3:1, or 4:1 (v/v) mixture of autologous ascites fluid and gel. In some embodiments, the biocompatible matrix comprises a 1:1 mixture of MATRIGEL and autologous ascites fluid.

The biocompatible matrix can be on a suitable culture surface. The thickness of the coating is not limiting. In some embodiments, the coating has a thickness of at least 0.5 mm. In some embodiments, the coating has a thickness of about 1 mm, 2 mm, 3 mm, or 4 mm. In some embodiments, the coating has a thickness of about 1 to 4 mm.

Media comprising ascites fluid from the subject can comprise 100% autologous ascites fluid with or without one or more suitable antibiotics. The antibiotic that can be added is not limiting. In some embodiments, the antibiotic is one that is commonly used in cell culture techniques, such as, for example, penicillin or streptomycin. In some embodiments cefoperazone is added to the media (Pfizer Dalian Pharmaceutical Plant) to a final concentration of 20 µg/ml. In some embodiments, the media comprises about 100%, about 95%, about 90%, about 85%, about 80%, about 75%, about 70%, about 65%, about 60%, about 55%, or about 50% (v/v) autologous ascites fluid. In some embodiments, a base media is combined with the autologous ascites fluid. The base media is not limiting, and can include, for example, saline, phosphate buffered saline, Dulbecco's Modification of Eagle's Medium (DMEM), Ham's F-12 (F12), Ham's F-10 (F10), RPMI 1640, Iscove's Modified Dulbecco's Medium (IMDM), or a combination thereof. In some embodiments, exogenous factors, such as antibodies, growth factors, cytokines, or FBS are not added to media and the cells are nourished primarily by the autologous ascites fluid without artificial modification.

Autologous ascites fluid can be obtained by any suitable means. In some embodiments, the autologous ascites fluid is obtained by filtration and/or centrifugation of ascites fluid. In some embodiments, autologous ascites fluid is obtained by centrifuging ascites fluid obtained from the patient to pellet cells contained in the ascites fluid at 2000 rpm followed by removing the ascites fluid supernatant and filtering the supernatant through a grade GF/F glass microfiber filter (Sigma-Aldridge Cat #WHA 1825025), followed by a 250-ml filter unit with 0.45µ filter (Fisher Scientific, Cat #09-740-24B) after adding cefoperazone to a final concentration of 20 µg/ml.

Culturing times and conditions are not limiting. In some embodiments, the cells are cultured for 3-4 days and then the media is refreshed. In some embodiments, the cells are passaged after digestion with a cell dissociation enzyme to release the cells from the biocompatible matrix. In some embodiments, the cells can be cultured for at least 1, 2, 3, 4, 5, 6, 7, 8, 9, 10, 11, 12, 13, 14, 15, 20 or 30 days.

In some embodiments, the method comprises:
coating a culture surface with a composition comprising one or more types of cell matrix proteins;
adding cells onto the coated surface, which cells are suspended in the ascites fluid from the subject; and
optionally adding a composition comprising more ascites fluid to continue the culture.

The composition comprising one or more cell matrix proteins is not limiting. The composition comprising one or more cell matrix proteins can comprise the biocompatible matrix described herein. In some embodiments, the composition comprising one or more cell matrix proteins is a 1:1 (v/v) mixture of MATRIGEL and autologous ascites fluid. In some embodiments, the composition comprising one or more cell matrix proteins is coated at a thickness of at least 0.5 mm on the culture surface. In some embodiments, the composition has a thickness of about 1 to 4 mm.

The cells can be cultured for any suitable period and is not limiting. In some embodiments, the cells are cultured for any period as described herein. The ascites fluid can be refreshed at any suitable time and is not limited. In some embodiments, a composition comprising ascites fluid is refreshed every 3-4 days.

Culturing Primary Cells from Pleural Effusion in Autologous Pleural Effusion Fluid In one embodiment, the invention provides a method of culturing primary cells from pleural effusion fluid from a subject comprising
i) obtaining the cells from pleural effusion fluid from the subject;
ii) seeding the cells on a surface of a biocompatible matrix; and
iii) culturing the cells in a media comprising pleural effusion fluid from the subject.

Pleural effusion fluid can be collected from the patient in any suitable amount. In some embodiments, 100-2000 ml of pleural effusion is collected from the patient. In other embodiments, 500-800 ml pleural effusion fluid is collected from the patient. Cells can be obtained from the pleural effusion fluid by any suitable means including centrifugation, density gradient centrifugation and filtration. In some embodiments, cells present in the collected pleural effusion fluid are pelleted by centrifugation, re-suspended in PBS, subjected to density gradient centrifugation in FICOLL, washed in PBS and re-suspended in autologous media comprising autologous pleural effusion fluid. In some embodiments, other types of density gradient centrifugation media can be used, like PERCOLL. In some embodiments, centrifugation is performed at 2000 rpm.

Any suitable amount of cells from the pleural effusion fluid can be seeded on the surface of the bio-compatible matrix. In some embodiments, about $1\times10^5$, $2\times10^5$, $3\times10^5$, $4\times10^5$, $5\times10^5$, $6\times10^5$, $7\times10^5$, $8\times10^5$, $9\times10^5$, or $1\times10^6$ cells are seeded on the surface of a biocompatible matrix coating a 100 mm culture dish or other type of culture plate or dish.

The cells can comprise noncancerous or cancerous cells and is not limiting. In some embodiments, the cells comprise cancer cells. The cancer cells can comprise stomach cancer cells, endometrium cancer cells, ovarian cancer cells, breast cancer cells, pancreatic cancer cells, uterine cancer, colon cancer cells, melanoma cells, leukemia cells, or lymphoma cells. The cells can comprise a mixed population of cells present in the ascites fluid. The mixed population can comprise cancer cells, blood cells and mesothelial cells at various proportions.

The biocompatible matrix can be any biocompatible matrix described herein. In some embodiments, the biocompatible matrix comprises one or more cell matrix proteins. In some embodiments, the cell matrix proteins comprise one or more of laminin, entactin, collagen, nidogen, or heparan sulfate proteoglycans.

In some embodiments, the biocompatible matrix comprises a gel. In some embodiments, the biocompatible matrix comprises a gel and autologous pleural effusion fluid. In some embodiments, the gel is MATRIGEL. In some embodiments, the biocompatible matrix comprises a mixture of MATRIGEL and autologous pleural effusion fluid. In some embodiments, the biocompatible matrix comprises a 1:1, 1:2, 1:3, 1:4, 2:1, 3:1, or 4:1 (v/v) mixture of a gel and autologous pleural effusion fluid. In some embodiments, the biocompatible matrix comprises a 1:1 (v/v) mixture of MATRIGEL and autologous pleural effusion fluid.

The biocompatible matrix can be a coating on a suitable culture surface. The thickness of the coating is not limiting. In some embodiments, the coating has a thickness of at least 0.5 mm. In some embodiments, the coating has a thickness of about 1 mm, 2 mm, 3 mm, or 4 mm. In some embodiments, the coating has a thickness of about 1 to 4 mm.

Media comprising pleural effusion from the subject can comprise 100% autologous pleural effusion fluid with or without one or more suitable antibiotics. The antibiotic that can be added is not limiting. In some embodiments, the antibiotic is one that is commonly used in cell culture techniques, such as, for example, penicillin or streptomycin. In some embodiments, cefoperazone is added to the media (Pfizer Dalian Pharmaceutical Plant) to a final concentration of 20 μg/ml. In some embodiments, the media comprises about 100%, about 95%, about 90%, about 85%, about 80%, about 75%, about 70%, about 65%, about 60%, about 55%, or about 50% (v/v) autologous pleural effusion fluid.

Autologous pleural effusion fluid can be obtained by any suitable means. In some embodiments, the autologous pleural effusion fluid is obtained by filtration and/or centrifugation of pleural effusion fluid obtained from a patient to remove cells present in the pleural effusion fluid. In some embodiments, autologous pleural effusion fluid is obtained by centrifuging pleural effusion fluid obtained from the patient to pellet cells contained in the pleural effusion fluid at 2000 rpm followed by removing the pleural effusion fluid supernatant and filtering the supernatant through a grade GF/F glass microfiber filter (Sigma-Aldridge Cat #WHA 1825025), followed by a 250-ml filter unit with 0.45μ filter (Fisher Scientific, Cat #09-740-24B) after adding cefoperazone to a final concentration of 20 μg/ml.

Culturing times and conditions are not limiting. In some embodiments, the cells are cultured for 3-4 days and then the media is refreshed. In some embodiments, the cells are passaged after digestion with a cell dissociation enzyme to release the cells from the biocompatible matrix. The cells can be cultured for at least 1, 2, 3, 4, 5, 6, 7, 8, 9, 10, 11, 12, 13, 14, 15, 20 or 30 days.

In some embodiments, the method comprises:
 coating a culture surface with a composition comprising one or more cell matrix proteins;
 adding cells onto the coated surface, which cells are suspended in the pleural effusion fluid from the subject; and
 optionally adding a composition comprising more pleural effusion fluid to continue the culture.

The composition comprising one or more cell matrix proteins can comprise a biocompatible matrix described herein. In some embodiments, the composition comprising one or more cell matrix proteins is a 1:1 mixture of MATRIGEL and autologous pleural effusion fluid. In some embodiments, the composition comprising one or more cell matrix proteins is coated at a thickness of at least 0.5 mm on the culture surface. In some embodiments, the coating has a thickness of about 1 mm, 2 mm, 3 mm, or 4 mm. In some embodiments, the coating has a thickness of about 1 to 4 mm.

The cells can be cultured for any suitable period and is not limiting. In some embodiments, the cells are cultured for any period as described herein. The pleural effusion can be refreshed at any suitable time and is not limited. In some embodiments, pleural effusion is refreshed every 3-4 days.

Culturing Cells from Blood in Autologous Serum

In one embodiment, the invention provides a method of culturing cells from blood from a subject comprising
 i) obtaining the cells from the blood of the subject;
 ii) obtaining serum from the subject; and
 iii) culturing the cells in the presence of a media comprising at least 50% (v/v) of the serum.

Obtaining cells from blood of the subject can be by any conventional means and is not limited. In some embodiments, cells are obtained by centrifuging an anti-coagulate treated blood sample to pellet the cells. In some embodiments, the cell pellet is further purified by density gradient centrifugation. In some embodiments, FICOLL can be used for density gradient centrifugation. In some embodiments, other types of density gradient centrifugation media can be used, like PERCOLL.

In some embodiments, the cells from the blood of the subject comprise a mixture of cell populations present in blood. In some embodiments, the cells from the blood of the subject comprise cancerous and noncancerous cells. In some embodiments, the cells from the blood of the subject comprise PBMC. In some embodiments, the cells from the blood of the subject comprise CTC. In some embodiments, the cells from the blood of the subject comprise CTC and PBMC. In some embodiments, the CTC comprise cancer cells selected from the group consisting of lung cancer cells, stomach cancer cells, colon cancer cells, lymph node metastatic cancer cells, melanoma cells, renal cell carcinoma cells, squamous non-small cell lung (NSCLC) cells, non-squamous NSCLC cells, rectal cancer cells, prostate cancer cells, ovarian cancer cells, hepatocellular carcinoma cells, pancreatic carcinoma cells, squamous cell carcinoma cells of the head and neck, esophageal cancer cells, gastrointestinal tract cancer cells, breast cancer cells, bone cancer cells, brain cancer cells, thyroid cancer cells, testicular cancer cells and vaginal cancer cells.

The method of obtaining the serum from the subject for use in the invention can be by conventional means and is not limiting. In some embodiments, 10-15 ml of fresh blood with anti-coagulant is withdrawn from each patient and is centrifuged to precipitate blood cells and collect the serum. In some embodiments, about 5 ml, 10 ml, 15 ml, 20 ml or 25 ml of fresh blood with anti-coagulant is withdrawn from each patient and is centrifuged to precipitate blood cells and collect the serum. One or more antibiotics can be added to the serum. The antibiotic that can be added is not limiting. In some embodiments, the antibiotic is one that is commonly used in cell culture techniques, such as, for example, penicillin or streptomycin. In some embodiments, cefoperazone is added to the serum (Pfizer Dalian Pharmaceutical Plant) to a final concentration of 20 μg/ml.

In some embodiments, the cells are cultured in a media comprising 50-100% (v/v) serum from the subject. In some embodiments, the cells are cultured in a media comprising about 50%, about 55%, about 60%, about 65%, about 70%, about 75%, about 80%, about 85%, about 90%, about 95%, or about 100% (v/v) serum from the subject. In some embodiments, a base media is combined with the subject's serum. The base media is not limiting, and can include, for example, saline, phosphate buffered saline, Dulbecco's Modification of Eagle's Medium (DMEM); Ham's F-12 (F12); Ham's F-10 (F10); RPMI 1640; Iscove's Modified Dulbecco's Medium (IMDM); or a combination thereof. In some embodiments, the media comprises a 1:1 mixture of the subject's serum and RPMI 1640. In some embodiments, the media comprises about a 1:1, 1:2, 1:3 or 1:4 (v/v) mixture of RPMI 1640 and the subject's serum. In some embodiments, exogenous factors, such as antibodies, growth factors, cytokines, or FBS are not added to media and the cells are nourished by the natural body fluid without artificial modification.

In some embodiments, about $1\times10^5$, $2\times10^5$, $3\times10^5$, $4\times10^5$, $5\times10^5$, $6\times10^5$, $7\times10^5$, $8\times10^5$, $9\times10^5$, or $1\times10^6$ cells per well of cells obtained from blood are cultured in a 24 well culture plate in media comprising autologous serum. In some embodiments, the cells are cultured in media comprising autologous serum for at least 1, 2, 3, 4, 5, 6, 7, 8, 9 or 10 or more days. In some embodiments, PMBCs are cultured in media comprising autologous serum for 4-5 days.

In some embodiments, blood is collected from a cancer patient and a cell population comprising PBMCs and CTCs are cultured in media comprising at least 50% autologous serum. In some embodiments, blood is collected from a cancer patient and a cell population comprising PBMCs and CTCs are cultured in media comprising 100% autologous serum.

In some embodiments, the invention provides a method of enriching circulating tumor cells (CTCs) in a population of blood cells, comprising
    obtaining a cell fraction comprising PBMCs from the blood of the subject;
    obtaining serum from the subject; and
    culturing the cells in the presence of serum from the subject for a period of time whereby the CTCs are enriched in the cell population.

In some embodiments, culturing cells in the presence of serum comprises culturing the cells in media comprising autologous serum as described herein. In other embodiments, the cells are cultured in 100% serum with or without added antibiotics as described herein.

The cells can be cultured for any suitable amount of time and is not limiting. In some embodiments, the cells are cultured for 1, 2, 3, 4, 5, 6, 7, 8, 9, 10, 15, 20, 25, or 30 days or more. In some embodiments, the CTCs are enriched by at least 1-fold, 2-fold, 3-fold, 4-fold, 5-fold, 10-fold, 20-fold, 50-fold, 100-fold, 500-fold or 1000-fold or more.

Methods of Testing the Toxicity or Effectiveness of a Therapeutic Agent and Methods of Treating Cancer In one embodiment, the invention provides a method for testing the effectiveness or toxicity of a therapeutic agent, comprising:
    i) culturing cells or solid tissue from a subject according to any of the methods taught herein,
    ii) contacting the cultured cells or solid tissue with the therapeutic agent, and
    iii) assessing the effectiveness or toxicity of the therapeutic agent as a treatment for the subject.

In some embodiments, the methods further comprise administering an effective amount of the therapeutic agent to the subject to treat a disease or condition if the therapeutic agent shows efficacy.

In one embodiment, the invention provides a method of treating cancer in a subject, comprising
    i) culturing cancer cells or solid cancer tissue from a subject according to any of the methods described herein;
    ii) contacting the cultured cells or solid tissue with a therapeutic agent;
    iii) assessing the effectiveness or toxicity of the therapeutic agent as a treatment for the subject; and
    iv) administering to the subject an effective amount of the therapeutic agent.

Culturing cells or solid tissue can be by any method taught herein using autologous fluid or serum. The cells or solid tissue can be any taught herein and can comprise cancerous or noncancerous cells or solid tissue. The cells or solid tissue can be contacted with the therapeutic agent at any suitable time and is not limiting. In some embodiments, the therapeutic agent can be contacted with the cells or solid tissue immediately or after about 1, 2, 3, 4, 5, 6, 7, 8, 9, or 10 days of culturing of the cells or solid tissue by the methods taught herein. The concentration of therapeutic agent contacted with the cells or solid tissue is not limiting. In some embodiments, a therapeutically effective amount of the therapeutic agent is contacted with the cells or solid tumor.

The therapeutic agent is not limiting. The therapeutic agent can be used to treat a disease or condition in a subject. The disease or condition is not limiting. In some embodiments, the therapeutic agent could be chemotherapy (as listed below), immunotherapy, gene therapy or other types of targeted therapies.

In some embodiments, the therapeutic agent is a cancer therapeutic selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Di sodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Di sodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate). In some embodiments, the drug is selected from the group consisting of Paclitaxel, Curcumin, Docetaxel, Ixabepilone, Vinblastine, Colchicine, Y-27632 Fasudil, SU6656 Dasatinib, HDAC inhibitors, ROCK inhibitors, Parthenolide, Costunolide and ML-7 Jazplakinolide.

The effectiveness or toxicity of the therapeutic agent as a treatment for the subject can be assessed by any suitable means and is not limiting. In some embodiments, the effectiveness or toxicity of the therapeutic agent as a treatment for the subject is assessed by microscopy, special staining (histochemistry), fluorescent labeling, radiation material labeling, and/or various cell apoptosis and viability assays.

In some embodiments, the cells or solid tissue comprises cancer cells from solid tumor and the effectiveness of the therapeutic agent as a cancer treatment for the subject is assessed. In some embodiments, cells comprise PBMC and the toxicity of the therapeutic agent for the subject is assessed. In some embodiments, the cells comprise CTC and the effectiveness of the therapeutic agent as a cancer treatment for the subject is assessed. In some embodiments, the cells comprise cancer cells obtained from ascites fluid or pleural effusion fluid and the effectiveness of the therapeutic agent as a cancer treatment for the subject is assessed.

A Method of Screening for Anti-Cancer Agents

In one embodiment, the invention provides a method of screening for anti-cancer agents, comprising
i) culturing cells or solid tissue from a subject according to according to any of the methods taught herein;
ii) contacting the cells or solid tissue with one or more candidate anti-cancer agents; and
iii) assessing the effectiveness or toxicity of the candidate anti-cancer agent as a cancer treatment.

Culturing cells or solid tissue can be by any method taught herein using autologous fluid or serum. The cells or solid tissue can be any taught herein. The cells or solid tissue can comprise cancerous or noncancerous cells. The cells or solid tissue can be contacted with the one or more candidate anti-cancer agents at any suitable time and is not limiting. In some embodiments, the one or more candidate anti-cancer agents can be contacted with the cells or solid tissue immediately or after about 1, 2, 3, 4, 5, 6, 7, 8, 9, or 10 days of culturing of the cells or solid tissue by the methods taught herein.

In some embodiments, the effectiveness or toxicity of the candidate anti-cancer agent as a cancer treatment is assessed by any suitable means and is not limiting. In some embodiments, the effectiveness or toxicity of the candidate anti-cancer agent as a cancer treatment is assessed by microscopy, special staining (histochemistry), fluorescent labeling, radiation material labeling, and/or various cell apoptotic and viability assays.

In some embodiments, the cells or solid tissue comprises cancer cells from solid tumor and the effectiveness of the candidate anti-cancer agent as a cancer treatment is assessed. In some embodiments, cells comprise PBMC and the toxicity of the candidate anti-cancer agent is assessed. In some embodiments, the cells comprise CTC and the effectiveness of the candidate anti-cancer agent as a cancer treatment is assessed. In some embodiments, the cells comprise cancer cells obtained from ascites fluid or pleural effusion fluid and the effectiveness of the candidate anti-cancer agent as a cancer treatment is assessed.

Methods of Testing the Toxicity and Effectiveness of a Therapeutic Agent

In one embodiment, the invention provides a method for simultaneously testing the toxicity and effectiveness of a therapy in order to select the treatment that is suitable for a subject, comprising
i) culturing cells or tissue according to any of the methods taught herein;
ii) contacting the cells or solid tissue with one or more candidate therapeutic agents; and
iii) assessing the effectiveness of the candidate therapeutic agents of ii); iv) culturing PBMC according to any of the methods taught herein;
v) contacting the PBMC with the one or more candidate therapeutic agents of ii);
vi) assessing the toxicity of the candidate therapeutic agents on the PBMC; and
vii) administering to the subject the therapeutic agent that exhibits therapeutic effectiveness against the cancer and low toxicity to the PBMC.

In some embodiments, the therapeutic agent is an anti-cancer agent. The anti-cancer agent is not limiting and can include any of the anti-cancer agents described herein.

The cells or solid tissue can be cultured with autologous serum or fluid by any method taught herein. The cells or solid tissue can be any taught herein and can comprise cancerous or noncancerous cells or solid tissue. The cells or solid tissue can be contacted with the one or more candidate therapeutic agents or anti-cancer agents at any suitable time and is not limiting. In some embodiments, the one or more candidate therapeutic agents or anti-cancer agents can be contacted with the cells or solid tissue immediately or after about 1, 2, 3, 4, 5, 6, 7, 8, 9, or 10 days of culturing of the cells or solid tissues by the methods taught herein.

In some embodiments, the effectiveness of the one or more candidate therapeutic agents or anti-cancer agents is assessed by any suitable means and is not limiting. In some embodiments, the effectiveness of the one or more candidate therapeutic agents or anti-cancer agents is assessed by microscopy, special staining (histochemistry), fluorescent labeling, radiation material labeling, and/or various cell apoptotic and viability assays.

The PBMC can be cultured with autologous serum or fluid by any method taught herein. The PBMC can be contacted with the one or more candidate therapeutic agents or anti-cancer agents at any suitable time and is not limiting. In some embodiments, the one or more candidate therapeutic agents or anti-cancer agents can be contacted with the PBMC immediately or after about 1, 2, 3, 4, 5, 6, 7, 8, 9, or 10 days of culturing of the PBMC by the methods taught herein.

In some embodiments, the toxicity of the one or more candidate therapeutic agents or anti-cancer agents is assessed by any suitable means and is not limiting. In some embodiments, the effectiveness of the one or more candidate therapeutic agents or anti-cancer agents is assessed by microscopy, special staining (histochemistry), fluorescent labeling, radiation material labeling, and/or various cell apoptotic and viability assays.

The present invention is further illustrated by the following Examples. These Examples are provided to aid in the understanding of the invention and are not to be construed as a limitation thereof.

EXAMPLES

Example 1

Materials and Methods
Clinical Samples Information:

All clinical materials were collected from Dalian Central Hospital, Dalian, China, during 2014 and 2015. This study was approved and monitored under the hospital Humane Society and Research Committee (YN2014-023-01). Primary cultures were performed for fourteen solid tumors and thirteen serous tumors (malignant ascites and pleural effusions). The solid tumors were from seven male and seven female patients whose ages ranged from 40 to 80, with an average of 61. These patients were diagnosed clinically as stomach cancers (n=6), lung cancers (n=7), and lymph node metastatic cancer from a stomach cancer patient (n=1). For the lymph node metastatic cancer from a stomach cancer patient an enlarged lymph node (LN; 2.5×1×1 cm$^3$) was used. Pathology confirmed that the enlargement of this LN was caused by cancer metastasis. All these cases were confirmed as cancers by histopathology (Table 1). For serous tumors, samples were collected from seven male and six female patients (n=13) and specimens included ascites (n=8) or pleural effusions (n=5) (see Table 2). Most of these body liquids were hemorrhagic (500-800 ml) and were diagnosed clinically as cancer-generated body fluids (Table 2). Patients' ages in this group ranged from 25 to 87, with an average of 59. In addition, PBMC from seven cancer patients were isolated. The tumor types are listed in Table 3.

TABLE 1

Source of solid tumors

| Case# | Sex | Age | specimen | Pathology Dx |
|---|---|---|---|---|
| 1 | M | 68 | Stomach | Gastric poorly differentiated adenocarcinoma |
| 2 | F | 75 | Lung | Pulmonary adenocarcinoma |
| 3 | M | 62 | Lung | Pulmonary moderately/poorly differentiated adenocarcinoma |
| 4 | F | 80 | Stomach | Gastric mixed mucinous carcinoma and poorly differentiated adenocarcinoma |
| 5 | M | 51 | Stomach | Gastric mixed mucinous carcinoma and poorly differentiated adenocarcinoma |
| 6 | M | 40 | Stomach | Gastric mucinous carcinoma |
| 7 | M | 54 | Lung | Pulmonary well-differentiated adenocarcinoma |
| 8 | F | 69 | Stomach | Gastric mixed adenocarcinoma and mucinous carcinoma |
| 9 | F | 70 | Lymph node | Metastatic adenocarcinoma (stomach) |
| 10 | M | 62 | Stomach | Gastric poorly differentiated adenocarcinoma |
| 11 | F | 58 | Lung | Pulmonary well differentiated adenocarcinoma |
| 12 | F | 62 | Lung | Pulmonary well differentiated adenocarcinoma |
| 13 | M | 58 | Lung | Pulmonary well/modertely differentiated adenocarcinoma |
| 14 | F | 47 | Stomach | Gastric poorly differentiated adenocarcinoma |

TABLE 2

Samples from ascites and pleural effusions

| Case# | Sex | Age | Specimen/ml | Clinical Dx | Pathology Dx |
|---|---|---|---|---|---|
| 1 | M | 42 | Ascites/800 | Stomach cancer; two years post gastrostomy. Two months post chemo | Some cells proliferate actively (biopsy of endoscope) |
| 2 | F | 74 | Ascites/800 | Ovary carcinoma; two years post ovariectomy, two weeks post chemo | Ovary serous papillary cystic adenoma (biopsy of ovariosalpingectomy) |
| 3 | F | 60 | Ascites/800 | Endometrium carcinoma; one year post uteroectomy. | Poorly differentiated adenocarcinoma (biopsy of endometrium) |
| 4 | M | 46 | Ascites/300 | Stomach cancer; two years post gastrostomy. | Adenocarcinoma (Cytology) |
| 5 | F | 69 | Pleural effusion/200 | Lung cancer | Adenocarcinoma (Cytology) |
| 6 | M | 58 | Pleural effusion/500 | Pleural Mesothelioma | Pleural Mesothelioma (Cytology) |
| 7 | F | 87 | Pleural effusion/650 | Lung cancer | Adenocarcinoma (Cytology) |
| 8 | M | 60 | Ascites/750 | Stomach cancer | Consider adenocarcinoma (Cytology) |
| 9 | F | 61 | Pleural effusion/600 | Unknown reason | No tumor cell was found (Cytology) |
| 10 | F | 25 | Ascites/500 | Stomach cancer | Adenocarcinoma (Cytology) |
| 11 | M | 39 | Ascites/300 | Pancreatic cancer | Adenocarcinoma (Cytology) |
| 12 | M | 77 | Ascites/800 | Pancreatic cancer | Contains cancerous cells (Cytology) |
| 13 | M | 76 | Pleural effusion/600 | Lung metastatic cancer | ND. Consider stomach cancer (Clinic) |

TABLE 3

PBMC samples

| Case # | PBMC source (patient with cancer) | Serum type | *Days in culture |
|---|---|---|---|
| 1 | lung | HS/FBS | 8 |
| 2 | stomach | HS/FBS | 7 |
| 3 | breast | HS/FBS | 8 |
| 4 | lung | HS/FBS | 7 |
| 5 | breast | HS/FBS | 8 |
| 6 | stomach | HS/FBS | 8 |
| 7 | stomach | HS only | 10 |

HS: autologous human serum;
FBS: fetal bovine serum

Autologous Culture Medium Preparations:

Two types of autologous culture media (ACM) were prepared for tissue/cell cultures. For the cultures of solid tumors, 10-15 ml of fresh blood without anti-coagulant was withdrawn from each patient before anesthesia and stored at room temperature until coagulation was complete and tumors were removed surgically. The blood was then centrifuged at 2,000 rpm for 10 minutes. The resultant serum was then immediately transferred to a clean polypropylene tube (usually 8-10 ml), supplemented with cefoperazone (Pfizer Dalian Pharmaceutical Plant) to a final concentration of 40 μg/ml, and then stored at 4° C. until use. Most of the autologous plasma was 1:1 diluted in RPMI-1640 medium (with 50% human plasma) to serve as an autologous culture medium for individual solid tumor growth (s-ACM). The second type of ACM is from ascites or pleural effusions. After collection (FIG. 1, Step A), body fluids were aliquoted into 50-ml tubes and centrifuged to precipitate cells at 2,000 rpm at 4° C. for 10 min (FIG. 1, Step B). The resultant supernatants were further cleaned by passing them through a grade GF/F glass microfiber filter (Sigma-Aldridge Cat #WHA 1825025, FIG. 1, Step C), followed by a 250-ml filter unit with 0.45μ filter (Fisher Scientific, Cat #09-740-24B) (FIG. 1, Step E) after adding cefoperazone to a final concentration of 20 μg/ml. These solutions served as autologous culture medium (f-ACM) for cells isolated from body fluid for each corresponding patient. Extra f-ACM was stored in a freezer at −80° C.

Figure 2:
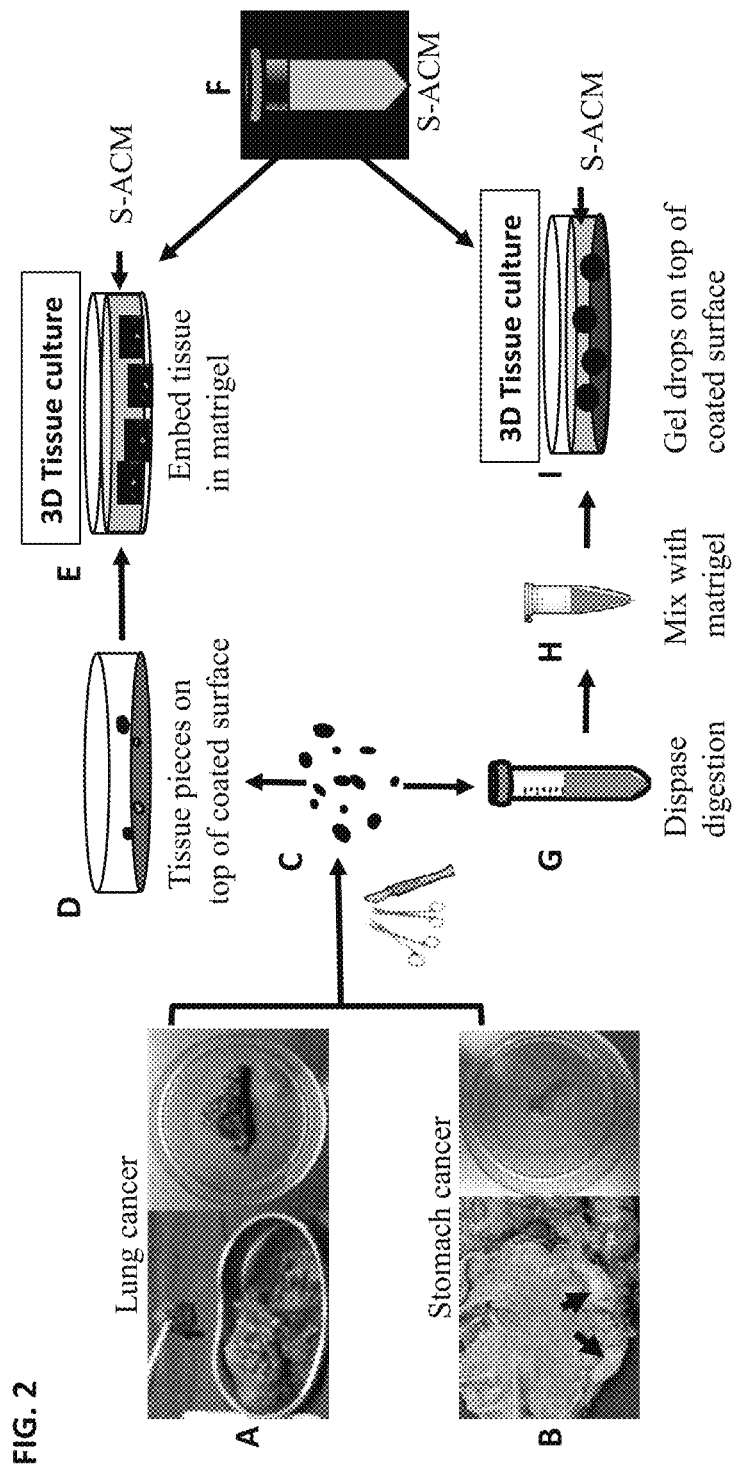
FIG. 2. Procedure for preparing tissue from solid tumors for culture. (A) Surgically removed tumor tissue from lung cancer. (B) Surgically removed tumor tissue from stomach cancer. (C) The tissues from lung or stomach cancer were cut into small pieces. (D) The small pieces were planted (3-4 pieces/well) on the surface, which was pre-coated with 1:1 diluted MATRIGEL (basement membrane matrix) in s-ACM, at a thickness of 0.5-1 mm. (E) Drops of the same gel were then placed on the tissue pieces to embed them in the coated surface. (F) After gel polymerization, s-ACM medium was added (upper procedure). (G) Other tumor pieces were digested in Dispase for 3D-cell culture. (H) These cells were counted and re-suspended in 1:1 cold autologous serum-MATRIGEL at a concentration of $1 \times 10^6$ cells/ml. (I) Gel-cell drops (30 µl/drop, 3-4 drops/well) were placed on top of the coated surface as mentioned above and after gel polymerization, s-ACM was added into the well (lower procedure).

Primary Cultures for Solid Tumors:

Wells in a pre-cooled 12- or 24-well plate were first evenly coated (≤0.5 mm in thickness) with MATRIGEL (basement membrane matrix) (BD Biosciences, Cat #356243) that was well-mixed with autologous plasma at a 1:1 ratio and polymerized in a 37° C. incubator for 30 min. Surgically removed tumor tissues (FIG. 2) were weighed, size-measured, and washed in cefoperazone-containing PBS (40 μg/ml) 3-5 times. Tissues were then cut into small pieces (≤0.5 mm in diameter), place on ice and covered with 1-2 drops of autologous serum to prevent drying. Three to four pieces of tumor tissue were placed into each pre-coated well and gently embedded in newly prepared MATRIGEL (basement membrane matrix) that was 1:1 diluted in cold s-ACM. The plate was then put into a 37° C. incubator for gel polymerization, to create a 3D environment for tumor growth. s-ACM medium was then added into the wells to completely cover the gel-embedded tissues (FIG. 2, upper procedure). Medium was refreshed every 3-4 days. Cultures with these small pieces of tumor tissues were designated as 3D-tissue cultures (in contrast to 3D-cell cultures).

To compare the culturing effects between 3D-tissue culture and previous, commonly used 3D-cell culture, part of the tumor pieces were digested in Dispase (BD Biosciences, Cat #354235) solution for 30-60 min while shaken, to obtain single cells suspension (FIG. 2, lower procedure). The resultant cell suspension was then passed through a 40 μm strainer to remove undigested tissue. RBC lysis buffer (ACK; ThermoFisher Scientific, Cat #A-10492) was used for samples containing too many red blood cells. After counting, cells were re-suspended in freshly prepared cold 1:1 autologous serum-MATRIGEL (basement membrane matrix); 3-4 drops were then placed in each well in the pre-cooled plate. After gel polymerization in a 37° C. incubator for 1 hour, s-ACM was added into the well (FIG. 2, lower procedure).

Primary Cultures of Cancer Cells from Ascites/Pleural Effusions:

A pre-cooled culture dish (100 mm) was first evenly coated (1-3 mm in thickness) with 1:1 diluted MATRIGEL (basement membrane matrix) in f-ACM and then placed in a 37° C. incubator for gel polymerization. Cell pellets from body fluids (FIG. 1, Step B) were re-suspended in 10-15 ml PBS and uploaded onto equal volumes of 75% FICOLL solution (TBD, Cat #LTS0770125), then spun at 2,000 rpm for 20 mins at room temperature to remove red blood cells. After collecting the cells from the enriched layer (FIG. 1, Step D), they were washed with PBS again and re-suspended in f-ACM before counting. Fifty thousand cells ($5 \times 10^5$)/plate in 10 ml of autologous f-ACM were seeded on top of the polymerized gel (FIG. 1, Step F) and the medium was refreshed every 3-4 days. For each cell passage, the same procedure was used as for primary cultures, after digestion with TRYPLE SELECT (cell dissociation solution) (GIBCO, Cat #12563-029).

Cultures of PBMCs from Cancer Patients:

Anticoagulants-treated 8-10 ml peripheral blood was centrifuged at 2,000 rpm for 10 mins. PBMC was isolated with routine FICOLL centrifugation protocol (TBD, Cat #LTS0770125). Cells were then seeded into a 24-well culture plate at $5 \times 10^5$/well. The growth conditions of cells were monitored and imaged with microscopy every day for 7-10 days. Autologous serum and commercial FBS were used individually as culture media; each condition was duplicated in both media for all time points, for comparison purposes. The cellular viability and total cells numbers were recorded daily.

Experimental Results and Discussion

Survival Rate of Primary Cultures:

A total of 27 clinical specimens were processed. After tissues or cells were seeded into culture wells, cell growth was monitored under microscope daily, and morphology images were taken at least every 2-3 days. Among all clinical specimens, the success rate for culturing cells isolated from ascites or pleural effusions (n=13) was nearly 100%, and for solid tumors (n=14) was 86% (Table 4 and Table 5).

TABLE 4

Summary of solid tumor cultures

| Case # | 3D cell culture | 3D tissue culture | *Days in autologous medium | *Days in FBS medium | Total days in culture |
|---|---|---|---|---|---|
| 1 | + | + | 8 |  | 8 |
| 2 | + | + | 16 | 10 | 26 |
| 3 | + | + | 15 | 10 | 25 |
| 4 | + | + | 15 | 10 | 25 |
| 5 | + | + | 14 |  | 14 |
| 6 | + | + | 13 |  | 13 |
| 7 | + | + | 8 |  | 8 |
| 8 | + | + | 8 |  | 8 |
| 9 | + | + | 8 |  | 8 |
| 10 | + | + | 4 |  | 4* |
| 11 |  | + | 8 |  | 8 |
| 12 |  | + | 6 |  | 6* |
| 13 |  | + | 15 | 14 | 29 |
| 14 |  | + | 20 | 6 | 26 |

*Culture was contaminated.

TABLE 5

Summary of body fluid sample cultures

| Case # | Days for confluent | Passages |
|---|---|---|
| 1 | 21 | 0 |
| 2 | 41 | 0 |
| 3 | 7 | 5 |
| 4 | 7 | 1 |
| 5 | 11 | 1 |
| 6 | 12 | 2 |
| 7 | 8 | 5 |
| 8 | 7 | 4 |
| 9 | 17 | 0 |
| 10 | 4 | 3 |
| 11 | 8 | 1 |
| 12 | 8 | 2 |
| 13 | 9 | 2 |

All 3D-tissue cultures (n=14) survived well for at least 8 days, except for two cases of contamination. The overall survival rate was 86%. Among the 14 samples, seven cultures were stopped before day-14 because of a shortage of s-ACM (Table 4). It is noteworthy that the duration of these cultures was mostly limited by either a shortage of s-ACM or by research requirements, not by cell growth failure.

Figure 3:
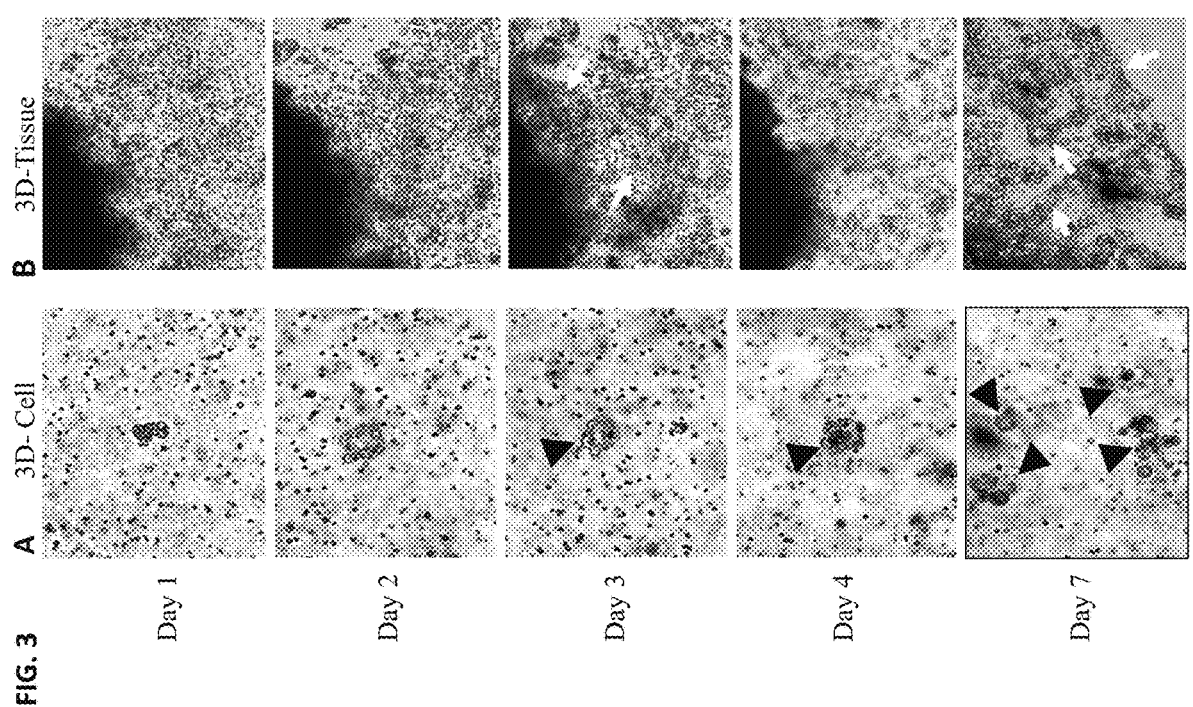
FIG. 3. Comparisons of lung cancers grown in 3D-cell culture (A) and 3D-tissue culture (B). Photomicrographs of 3D-cell culture (left column) and 3D-tissue cultures (right column) taken on days 1, 2, 3, 4 and 7 of culturing. Arrowheads in the left column (3D-cell culture) indicate dead and degenerated cells. Arrows in the right column (3D-tissue culture) show cells that, by day 3, started growing out of the initially planted tissue pieces, and that formed adenoid structures by day-7.
Figure 4:
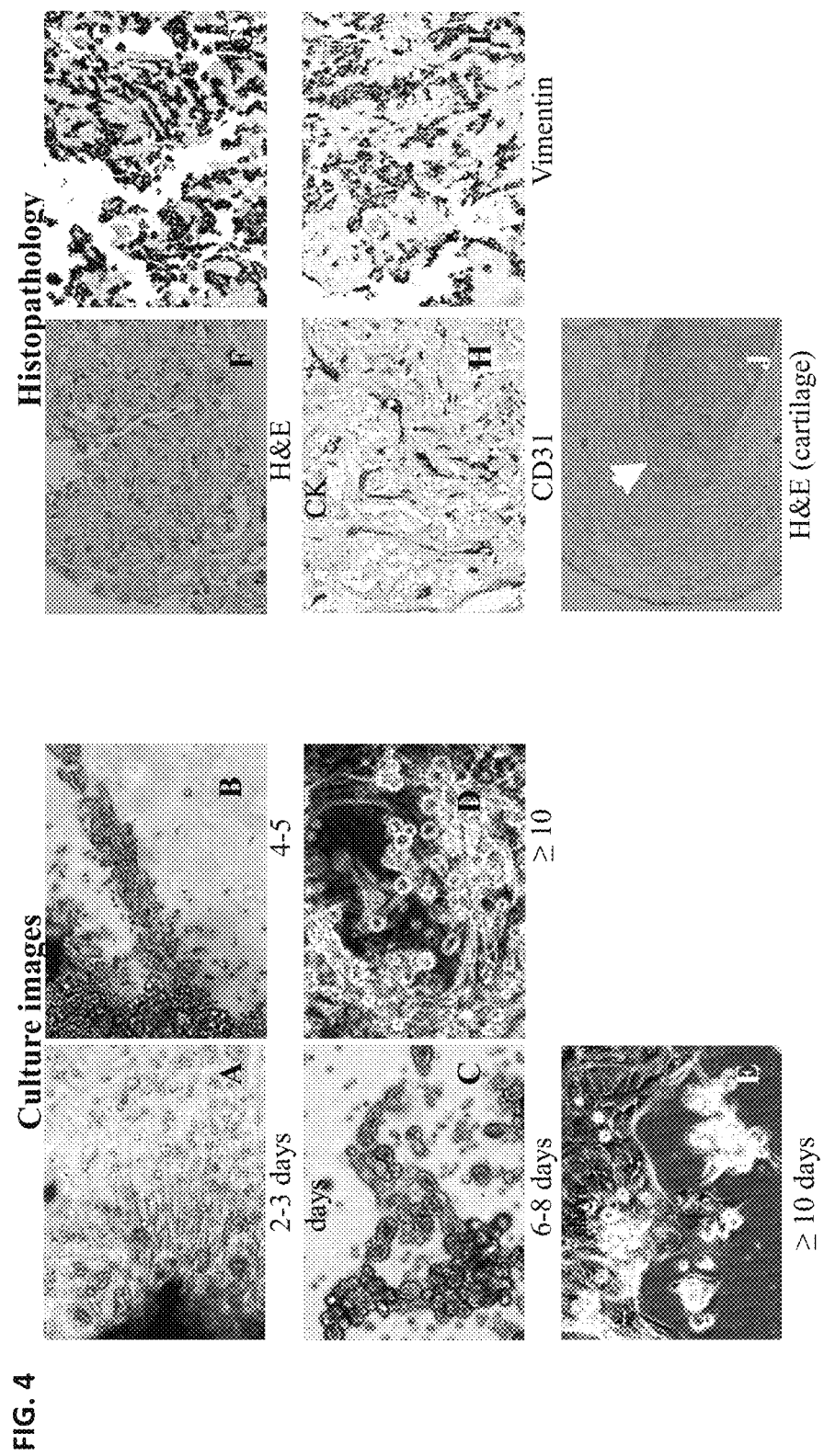
FIG. 4. Tissue re-formation and multiple types of cell survival in 3D-tissue cultures of lung cancer. (A-E) Photomicrographs of tissue culture on days 2-3 (A), 4-5 (B), 6-8 (C), and at or beyond 10 days (D and E). (F-J) Histopathology stains showing (F) hematoxylin and eosin staining (G) tumor cells (CK$^+$), (H) blood vessels (CD31$^+$), (I) other mesenchymal cells (Vimentin$^+$) and (J) cartilage tissue (H&E (cartilage)). The white arrow indicates surviving cartilage tissue from the tumor sample.

Cell growth conditions of the present 3D-tissue culture were compared to previously established 3D-cell culture. Among the 14 solid tumors processed, these two types of cultures were performed side by side in nine cases. Cells in 3D-cell cultures did not survive more than seven days. A gradual reduction in cell numbers was observed after day 3. At day 7, most of the cells had degenerated or were dead (FIG. 3, left column). In contrast, multiple types of cells in 3D-tissue culture grew out from the initial tissue plants at day 3, and tissue-like structures were observed between 5-7 days (FIG. 3, right column). FIG. 4 (left, "culture images") demonstrates the different structures that these cells formed in the culture wells. Histopathology stains confirmed that in addition to tumor cells ($CK^+$), blood vessels ($CD31^+$), other mesenchymal cells ($Vimentin^+$) and even cartilage tissue also survived in these cultures (FIG. 4, right, bottom, H&E). Staining occurred at the end-point of the culture when the serum was used up. This happened on different time-points for different tumors after the culture was started. This figure shows that in addition to the tumor cells, other types of tissue cells survive. All tumors that were cultured similarly contained various types of connective tissues. These results indicate that 3D-tissue cultures provided a better cell-growth condition, resulting in a greater survival rate than in 3D-cell cultures. The possible explanations for this are (1) for the 3D-cell culture, the additional procedures of enzyme digestion and ACK treatment after mechanical dissection might have caused more harm to cells, and (2) the intact tumor tissues in the 3D-tissue cultures provided a better microenvironment for the survival of various cells, and the latter assist and support tumor cells to form tissue structures that were similar to their original histopathology.

This primary culture technique for solid tumors provides many benefits that traditional and other previous tissue/cell cultures do not provide. When solid tumors grow in patients, they have special 3D tissue structures to allow tumor cells to communicate with each other and with other body cells. Sufficient blood supply provides not only nutrients but also other bio-chemicals that are required for tumor cell growth. The present culture technique maximally mimicked these physiological conditions. First, the culture is a multicellular environment composed of both tumor and their autologous surrounding tissue cells (FIG. 4). These cells can constantly communicate with each other via direct contact or matrix, and they are able to rebuild a similar histologic structure as the original tumor. Second, tumor cells inside their tissue structures grow three dimensionally. Third, the nutrient and blood chemicals were basically from a patient's own blood supply, which is highly individualized for a particular tumor. With the autologous culture medium, cytokines, lymphokines, growth factors and hormones maximally maintained levels similar to those for tumors inside of an individual patient. Because the living environment created was very close to the cells' physiological condition, both tumor cells and their surrounding "normal" cells were able to survive in culture for about 10 days with a limited amount of serum (10-15 ml of blood). Survival times are expected to be longer if more blood is available. Based on the observed morphology, cells are ready for drug-sensitivity testing within seven days in culture; this enables the testing to be conducted in a timely manner for the patient.

Figures 5A, 5B:
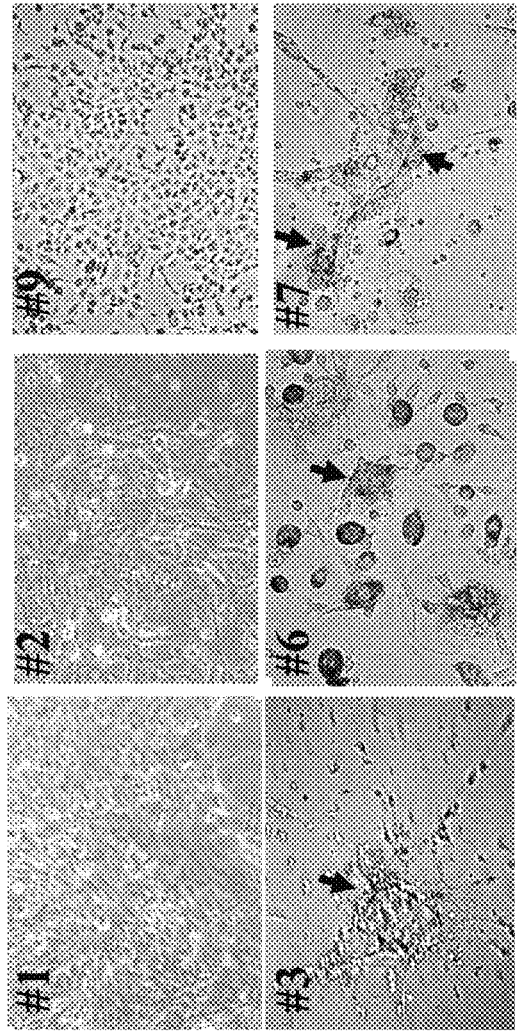
FIG. 5. Growth characteristics of tumor cells from ascites/pleural effusion. (A) shows photomicrographs of ascites/pleural effusion tumor cells from stomach cancer (#1), ovarian cancer (#2), and a patient without cancer (#9), endometrial cancer (#3), malignant mesothelioma (#6) and lung cancer (#7). (B) Summarizes the patient cancer samples and diagnosis. (C) Photomicrographs of ascites/pleural effusion tumor cells from pancreatic cancer (#12) and stomach metastatic cancer metastasizing to the lung (#13) on days 1, 5, 7 and greater than day 10. In the rightmost column of (C) are hematoxylin and eosin (H&E) stains for pancreatic cancer (#12, top image) and stomach metastatic cancer (#13, bottom image).

The survival rates for cells from ascites and pleural effusions were 100% (Table 5). There are also mixed populations in these body fluids, which contain tumor cells, blood cells, mesothelial cells, and possibly other type of cells in different proportions. Therefore, the time for cells to become confluent in a dish ranged from 4-41 days (Table 5), even though all cases were started with a similar amount of cells. Cells isolated from cases #1, #2, and #9 took a much longer time to become confluent in culture dishes than cells from other cases (Table 4). By reviewing treatment histories, it was apparent that patients #1 (21 days) and #2 (41 days) had received chemotherapy intraperitoneally not long before samples were taken. Additionally, it was suspected that patient #9 had tuberculosis, and no tumor cells were subsequently found in this patient by cytology. This explains the slow growth of these samples. Morphologically, most of the cells in these three cultures were more uniform in size and shape, with a large amount of fibers produced by cells in the dishes. This suggests that there were fewer or no tumor cells in the original samples, just different types of "normal" cells (FIG. 5A upper row). Although these cells survived in these culture conditions, they failed in passage to the next generation (Table 4). In comparison, cells in the other 10 cases grew faster, with an average time to confluence of 8 days, and none of these cases failed in passage (Table 5). Morphologically, cells in the cultures had very different shapes and sizes, indicating a mixture of large tumor cells and other type of cells (FIG. 5A lower row). Similar morphology was observed even after several passages. Although all these cultures started with single cell suspensions, cells tended to form tissue-like structures after 10 days in culture dishes (FIG. 5C).

The physiological conditions of cells isolated from ascites and pleural effusions are different as compared to those from solid tumors; therefore, the culture condition was modified accordingly. Generally, to survive, tumor cells floating in the ascites or pleural effusions need to penetrate the surface of the plasma membrane of a peritoneal or pleural cavity (transcoelomic metastasis). To mimic this physiological condition, we used f-ACM-MATRIGEL (basement membrane matrix) (1:1) coated plates and seeded the cells on top of the gel without embedding them in gel (FIG. 2). Cells then settled themselves down quickly on top of f-ACM-prepared MATRIGEL (basement membrane matrix) and grew in autologous body fluid. This culture condition is similar to that inside of patients' body cavities. As a result, all primary cultures with this type of sample were successful. In addition, because there was enough f-ACM to carry cells for a longer time and cell passages became available. For research purposes, cultures were stopped at different passages (Table 5) and cells were harvested and stored in liquid $N_2$. Recovery of cells from liquid $N_2$ was successfully performed in four samples (data not shown). These results indicate that almost all cells isolated from body liquid can survive in the present culture condition, including "normal" (non-cancerous) cells and cells recently treated with chemo; however, only in samples containing more tumor cells could the cells survive longer and pass to the next generation.

Figure 6A:
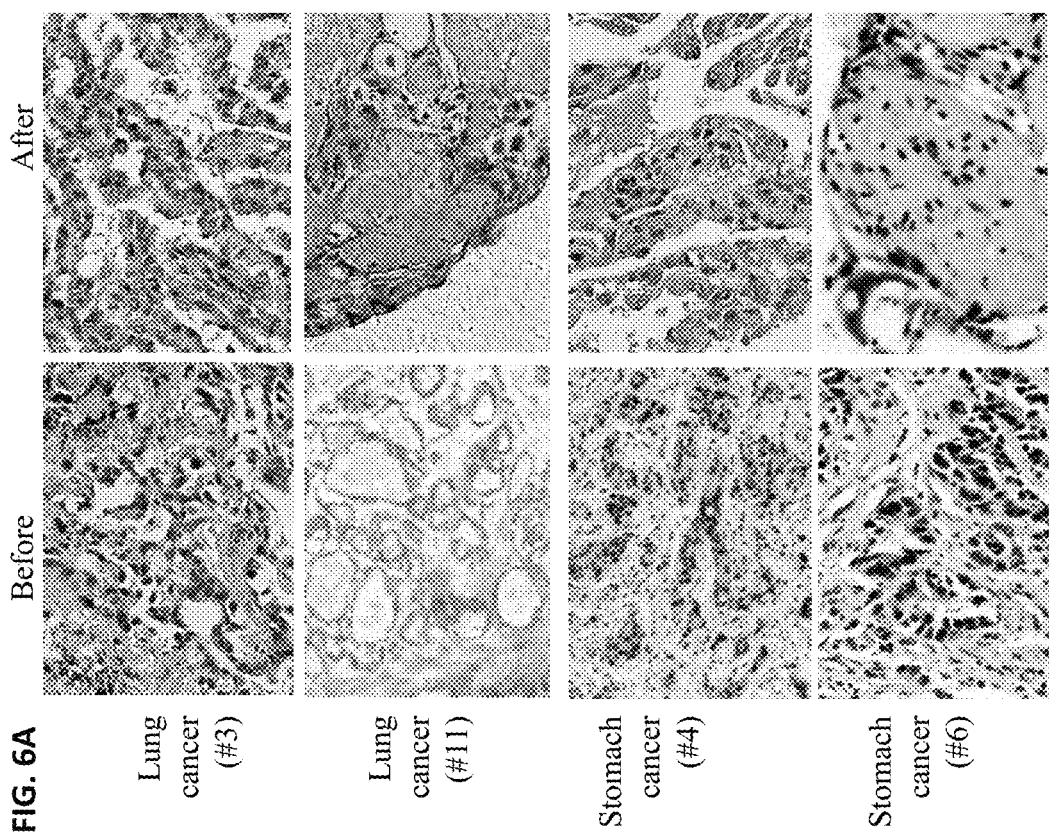
FIG. 6. Histopathology comparisons before and after cultures. (A) Hematoxylin and eosin (H&E) histopathology stains of solid tumors before culturing (left column) and after culturing (right column) for lung cancer (#3 and #11) and stomach cancer (#4 and #6). (B) H&E stains of serous tumors before culturing (left column) and after culturing (right column) for lung cancer (#7), stomach cancer (#8), pancreatic cancer (#12) and lung metastatic cancer (#13). Stains were generally done 8-16 days after the beginning of culturing, depending on the tumor growth condition, and are all "end-point" staining after fixation in formalin.
Figure 6B:
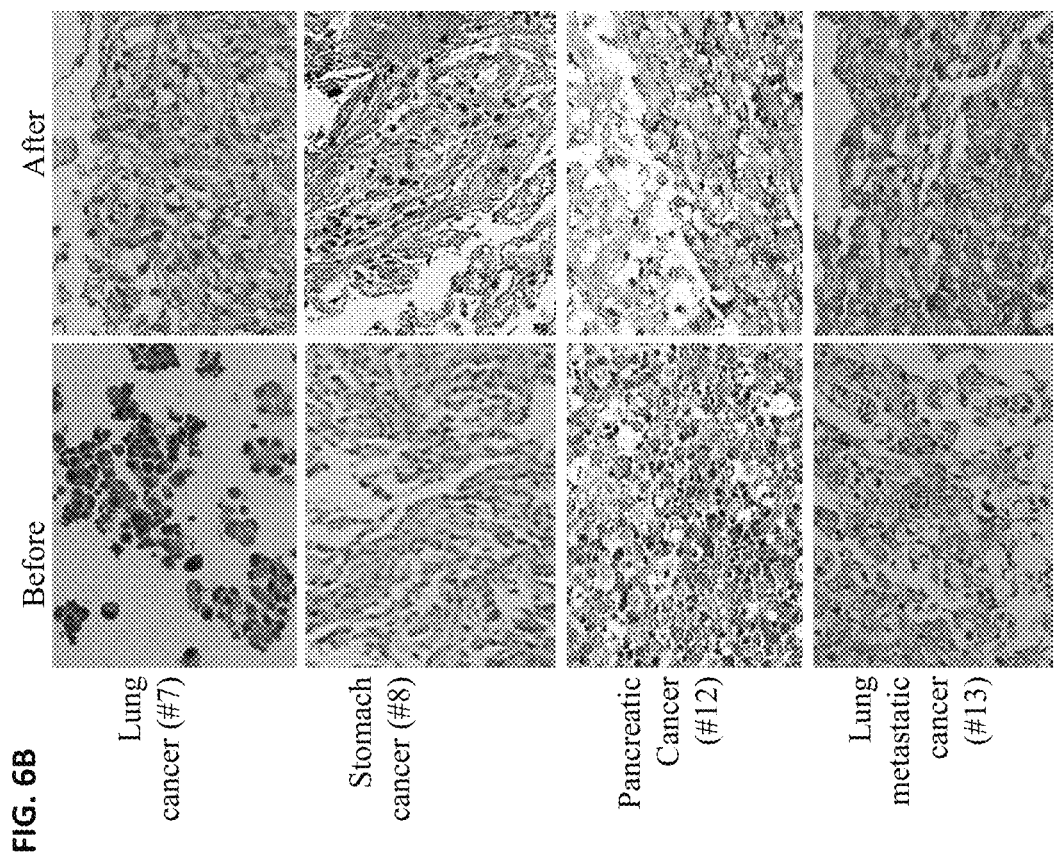

Histopathology Comparison Before and after Cultures:

Unlike in cultures previously reported by others, tumor cells grown in the present novel culture conditions preserved the ability to form tissue structures similar to what they were in human bodies. As shown in Table 1, all the solid tumors in the present studies were adenocarcinomas with different differentiation levels from either stomach or lung. Tumor cells in the culture wells showed a strong tendency to form adenoid structures (FIG. 6A, right column). Even more interesting is that adenocarcinoma cells isolated from serous cancers (in single cell suspension before being placed in cultures) also preserved the ability to form adenoid structures (FIG. 6B, right column; FIG. 5C, right column). This phenomenon strongly suggests that the natural characters and biological properties were well-maintained in the present culture system. Under this culture condition, tumor cells grow not alone but within complete tissue-like structures, where multiple surrounding cells that are in the original tumor microenvironment co-exist in the culture. These cells participate in the structure formation and play supporting roles for tumor survival and growth. The major difference between the present co-culture conditions and others is that all cells in the present culture conditions are autologous, in other words, from the same patient.

Figure 7A:
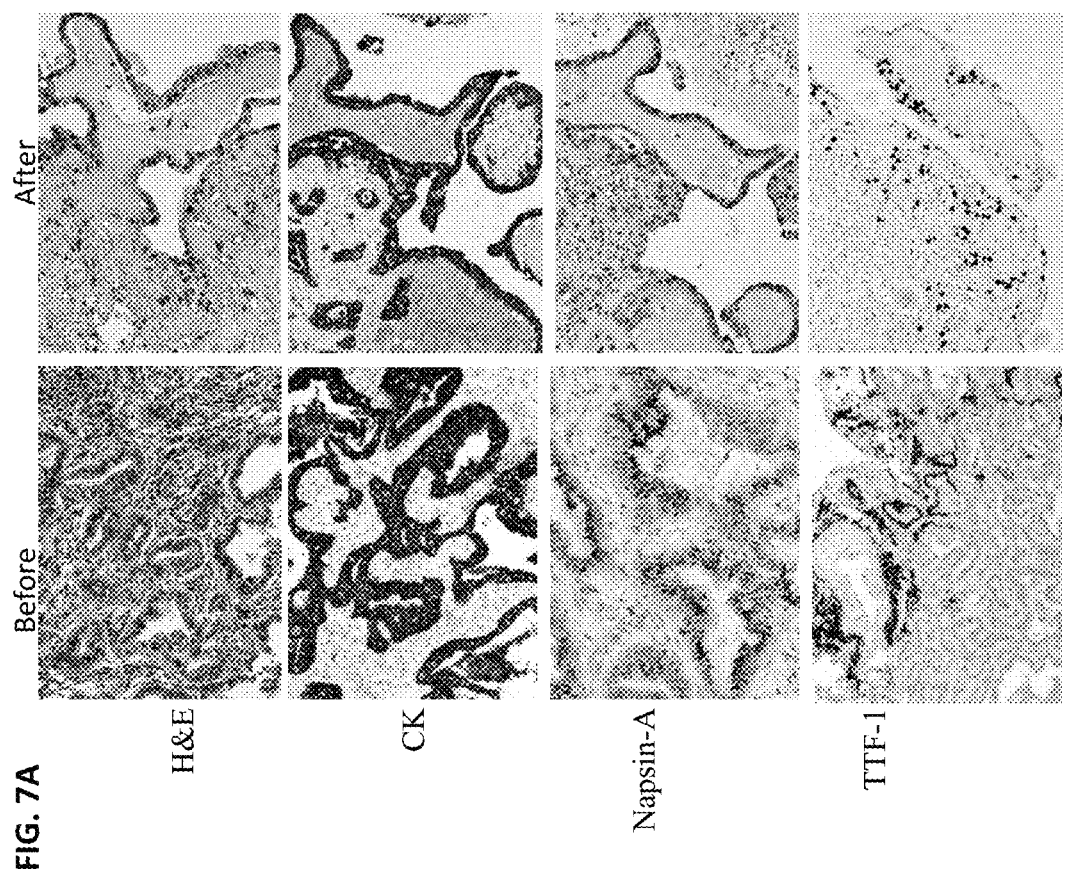
FIG. 7. Immunohistochemistry comparisons before and after cultures. (A) H&E (top two panels) and immunohistochemistry staining of lung cancer (solid tumor, Case #2) with antibodies against CK, Napsin-A, and TTF-1, prior to culturing (left column) and after culturing for 26 days (right column); in this case, FBS was added to the medium to extend the culture after 10 days in s-ACM. (B) H&E (top two panels) and immunohistochemistry staining of stomach cancer (solid tumor, Case #8) with antibodies against CK, CEA and CDX-2, prior to culturing (left column) and after culturing for 8 days (right column). 7C shows H&E (top two panels) and immunohistochemistry staining of lung cancer from pleural effusion (Case #7) with antibodies against CK and TTF-1, prior to culturing (middle column) and after two passages in culturing (P2) (right column). Collected pleural effusion specimen (D) Photomicrograph of the culture image at the second day of passage two (P2) of the lung cancer from pleural effusion. (E) Staining with H&E, CK and TTF-1 from the specimen before (left panels) and after passage (right panels). (F) Collected ascites specimen from endometrial cancer. (G) Photomicrograph of the culture image at the second day of passage four (P4) of the endometrial cancer from ascites specimen. (H) H&E (topmost panel) and immunohistochemistry staining of endometrial cancer from ascites (Case #3) after culturing for 4 passages with antibodies against CK and ER.
Figure 7B:
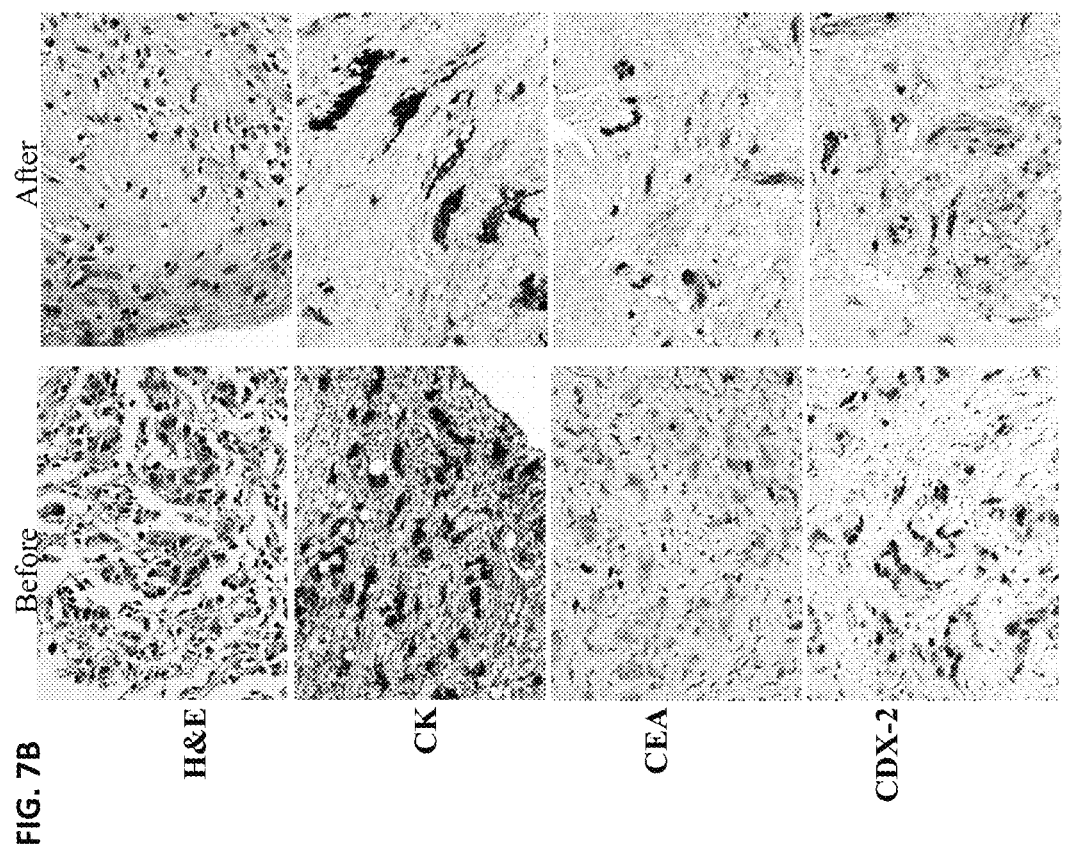
Figure 7E:
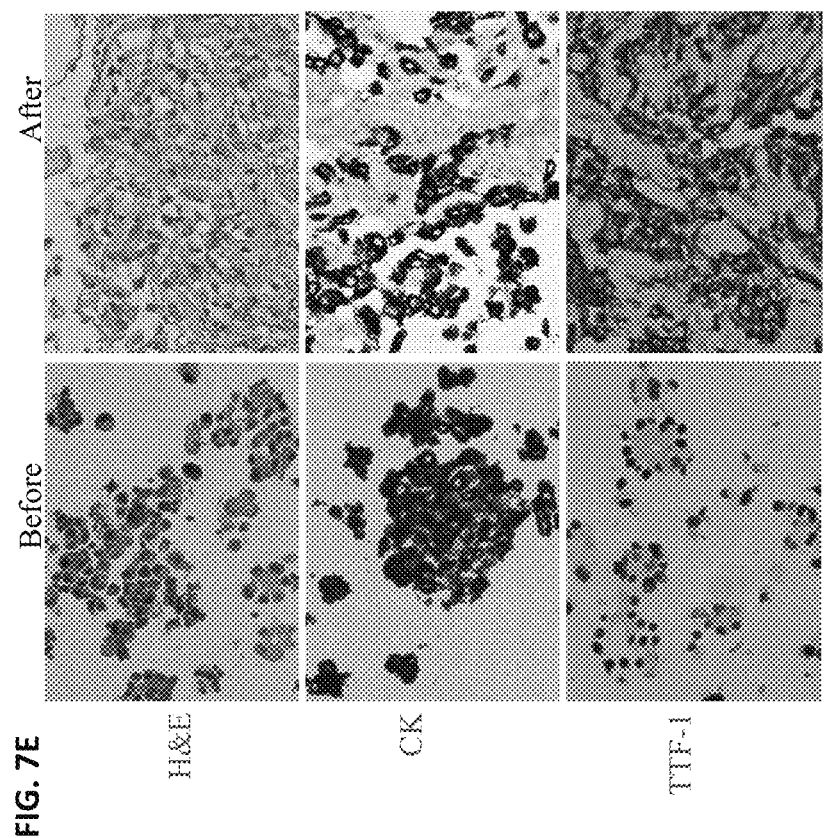
Figure 7C:
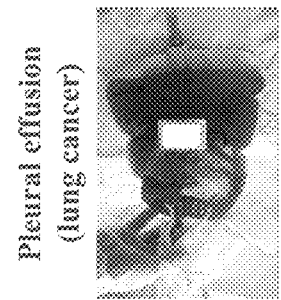
Figure 7D:
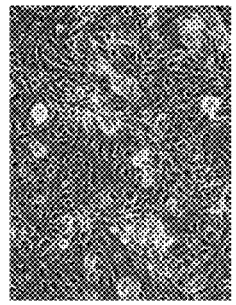
Figure 7H:
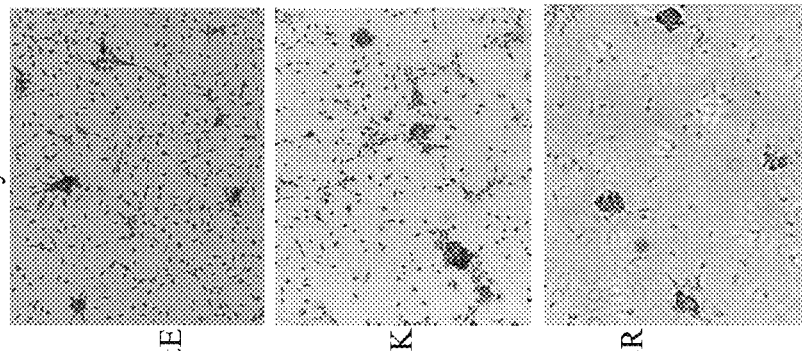
Figure 7F:
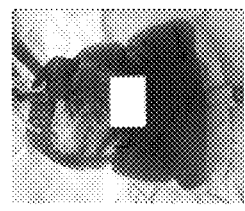
Figure 7G:
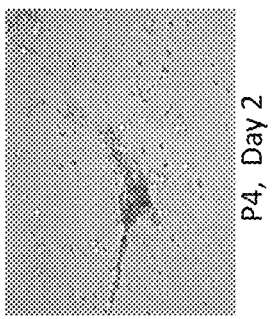

Immunophenotype Comparison Before and after Cultures:

Furthermore, cells in the present culture conditions were also highly consistent in their immunophenotypes before and after cultures. Immunohistochemistry (IHC) was performed in 10 samples (six solid tumors and four serous tumors) and the expressions of markers tested were compared in samples before and after cultures. Antibody against CK, Napsin-A, and TTF-1 were used in lung cancers (FIG. 7A) and CK, CEA and CDX-2 were used in stomach cancers (FIG. 7B). The expressions of these markers were unchanged in cultured cells relative to the original tissues. Similar results were observed in samples of serous cancers. Cells from pleural effusions of lung cancer expressed the same phenotypes when tested, even after two passages (FIG. 7E), and endometrial cancer cells stayed ER– (estrogen receptor) positive even after four passages (FIG. 7H).

PBMC and CTC Growing in Autologous Serum:

Two morphological differences between HS (autologous human serum) and FBS were observed in all seven samples tested. First, the red blood cells (RBC) in FBS showed damage within 48 hours and became aggregated and clumpy (FIGS. 8A and B, right column, arrowhead). In contrast, RBC in HS maintained their regular shape at all time points, even at day-10, if any RBC were left (data not shown), even though they tended to line up together (FIGS. 8A and B, left column, arrow). Second, in three of seven cases studied, a large number of tumor cells were observed by day-6 in HS culture wells, but not in the FBS-wells of the same sample (FIGS. 8C and D). These tumor cells were not visible in the cultures at 48-hour time points (FIGS. 8A and B), which indicates that they proliferated from a very small amount of CTCs in the patient's blood circulation. The morphological differences between PBMCs and CTCs growing in HS and FBS are consistent with those of solid tumor and serous cancer cells growing in s-ACM and f-ACM: both tumor cells and body cells survive better in autologous serum. PBMC cell counts showed nearly 100% cellular viability during the first four days in culture; the reduction in cell numbers started around day-5, which could be due to the natural life span of the blood cells. With limited number of cases, no significant differences were found in cellular viability between HS and PBS culture conditions. Based on above study, it is believed that most human peripheral blood cells could survive in autologous serum for at least 4-5 days, which provides an adequate testing window for drug toxicity. Chemo-toxicity causes sever immune depression which results in a significant reduction in white blood cell count, causing patients to die of various infections or infectious diseases. Using this culture system, it becomes possible to test the drug-sensitivity of a patient's PBMCs before drug administration. The best way to test the toxicity of a drug to the cancer patient would be using his/her bone marrow; the success of the present methods in primary cultures for different tumors and PBMCs suggests bone marrow cells should be able to survive well under this culture system.

To summarize, the high success rate of primary culture with this novel technique is due to three major factors: use of autologous body fluid, retention of multicellular communications and imitation of growth conditions in the body. With similar components and levels of various nutrients, growth factors, chemokines/cytokines, and hormones in autologous body fluid, both tumor and stroma cells easily adapted to the new but similar growth environment in vitro. In the present culture system, with the support of autologous tumor-surrounding cells, tumor cells grow not alone but as a tissue in which the physiological cellular communications in vivo are preserved. Because the CTCs' living condition remains the same, they also proliferate well. Since the present culture system maintains nearly the same conditions as tumors growing in the patients, drug-sensitivity testing can more accurately predict the tumors' responses in patients. Furthermore, the use of ACM is more cost-effective for cancer patients because no additional commercial cells, growth factors, or stimuli are needed in this culture system. Additionally, this culture system only requires a small amount of cells and body fluid, and so causes no harm to the patient.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

The invention claimed is:

1. A method for the primary culturing of cancer cells from the ascites or pleural effusion fluid of a subject, using the following steps in the order shown:
   A. obtaining the fluid from the subject;
   B. isolating the cells from the fluid while retaining the cell-free fluid;
   C. filtering the cell-free fluid to prevent protein clotting;
   D. building a three dimensional autologous structure by
      a) mixing one or more matrix proteins with the filtered, cell-free fluid at a ratio of approximately 1:1 to make an autologous matrix,
      b) coating the surface of a culture well or plate with the autologous matrix,
   E. seeding the isolated cells from step B onto the coated surface of step D; and
   F. culturing the seeded cells in a medium consisting essentially of 100% cell-free fluid (v/v) from step C.

2. A method for culturing circulating tumor cells (CTC) from the peripheral blood of a subject, using the following steps in the order shown:
   A. obtaining blood from the subject;
   B. isolating a cell population containing both CTC and the peripheral blood mononuclear cells (PBMC) from the subject's blood, while retaining the serum;
   C. building a three dimensional autologous structure by
      a) mixing one or more matrix proteins with the serum from step B at a 1:1 ratio to make an autologous matrix,
      b) coating the surface of a culture well or plate with the autologous matrix,
   D. seeding the cells from step B onto the coated surface of step C,
   E. culturing the seeded cells in a medium consisting essentially of 100% serum (v/v) from the subject.

3. The method of claim 1 or 2 wherein the cells are isolated using density gradient centrifugation.

4. The method of claim 1 or 2 wherein the thickness of the layer coating the well or plate is approximately one to four millimeters.

5. The method of claim 1 or 2 wherein the one or more matrix proteins comprises laminin, elastin, collagen, and heparin sulfate proteoglycans.

6. A method for the concurrent testing of the toxicity and effectiveness of candidate cancer therapies to select the treatment that is most suitable for a particular subject, comprising:
   A. culturing cells from the subject according to the method of claim 1 or 2, depending on the type of cells:
   B. obtaining blood from the subject, isolating PBMC from the blood by density gradient centrifuge, and maintaining the isolated PBMC in a medium consisting essentially of 100% serum (v/v) from the subject;
   C. applying the candidate therapy in parallel to the culture of step A and to the PBMC from step B, following the same treatment protocol;
   D. assessing the effectiveness of the candidate treatment against the cancerous cells in the culture from step A, and measuring the toxicity of the treatment to the PBMC from step B;
   E. selecting the therapy having the highest effectiveness against the cancer, and an acceptable toxicity to the PBMC from the subject.

7. The method of claim 6, step C wherein the candidate therapy comprises, but is not limited to, any chemical agent, targeted gene therapy product, immunotherapy product, radiation procedure or other anti-cancer regimen, applied singly or concurrently.

8. The method of claim 6, step D, wherein the effectiveness and toxicity of the candidate therapy is measured using one or more cell viability assays.

* * * * *